United States Patent
Anderson et al.

(10) Patent No.: US 12,209,228 B2
(45) Date of Patent: *Jan. 28, 2025

(54) 2-IN-1 SANITIZING AND RINSE AID COMPOSITIONS EMPLOYING AMINE BASED SURFACTANTS IN MACHINE WAREWASHING

(71) Applicant: ECOLAB USA INC., Saint Paul, MN (US)

(72) Inventors: Derrick Richard Anderson, Saint Paul, MN (US); Kelly Anne Rightmire, Saint Paul, MN (US); Erik C. Olson, Saint Paul, MN (US); Jesse Ray Murphy, Saint Paul, MN (US); Carter M. Silvernail, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/335,800

(22) Filed: Jun. 15, 2023

(65) Prior Publication Data
US 2024/0002750 A1 Jan. 4, 2024

Related U.S. Application Data

(63) Continuation of application No. 17/301,039, filed on Mar. 23, 2021, now Pat. No. 11,718,813.
(Continued)

(51) Int. Cl.
*C11D 1/40* (2006.01)
*A01N 25/00* (2006.01)
(Continued)

(52) U.S. Cl.
CPC ............... *C11D 1/835* (2013.01); *A61L 2/18* (2013.01); *C11D 3/38618* (2013.01);
(Continued)

(58) Field of Classification Search
CPC .... C11D 1/40; C11D 1/52; C11D 1/72; C11D 1/835; C11D 3/30; C11D 3/386;
(Continued)

(56) References Cited

U.S. PATENT DOCUMENTS

| | | | | |
|---|---|---|---|---|
| 5,276,047 A | * | 1/1994 | Eggensperger | ....... D06M 16/00 514/674 |
| 5,393,789 A | | 2/1995 | Eggensperger et al. | |

(Continued)

FOREIGN PATENT DOCUMENTS

DE 19918475 A1 10/2000
EP 0333143 A2 9/1989
(Continued)

OTHER PUBLICATIONS

"Product Information Lonzabac™ 12.100", Lonza Life Science Ingredients—Microbial Control Europe, 2 pages, Oct. 29, 2014.
(Continued)

*Primary Examiner* — Brian P Mruk
(74) *Attorney, Agent, or Firm* — McKee, Voorhees & Sease, PLC

(57) ABSTRACT

Sanitizing cleaning/rinse aid compositions for various applications including institutional machine warewash sanitizing are disclosed. In particular, concentrated and use compositions, such as concentrated liquid rinse aid compositions or ware wash detergents, employing an amine-based surfactant and a defoaming agent are disclosed. In particular, the present disclosure provides compositions and methods for providing a sanitizing rinse with desired antimicrobial efficacy against a broad spectrum of gram-negative microbes, suitable foaming profiles, and beneficial applications of use of the same.

17 Claims, 11 Drawing Sheets

Related U.S. Application Data

(60) Provisional application No. 62/993,172, filed on Mar. 23, 2020.

(51) Int. Cl.
| | |
|---|---|
| *A01N 33/04* | (2006.01) |
| *A01N 63/50* | (2020.01) |
| *A61L 2/18* | (2006.01) |
| *B08B 3/04* | (2006.01) |
| *C11D 1/52* | (2006.01) |
| *C11D 1/72* | (2006.01) |
| *C11D 1/835* | (2006.01) |
| *C11D 3/30* | (2006.01) |
| *C11D 3/386* | (2006.01) |
| *A61L 101/36* | (2006.01) |
| *C11D 1/74* | (2006.01) |

(52) U.S. Cl.
CPC ....... *A61L 2101/36* (2020.08); *A61L 2202/17* (2013.01); *C11D 1/40* (2013.01); *C11D 1/528* (2013.01); *C11D 1/74* (2013.01); *C11D 2111/14* (2024.01)

(58) Field of Classification Search
CPC ....... C11D 11/0023; B08B 3/04; A01N 25/00; A01N 33/04; A01N 63/50; A61L 2/18; A61L 2202/17
See application file for complete search history.

(56) References Cited

U.S. PATENT DOCUMENTS

| | | | | |
|---|---|---|---|---|
| 5,554,656 | A | 9/1996 | Löwer et al. | |
| 5,576,284 | A | 11/1996 | van Buskirk et al. | |
| 6,191,092 | B1 * | 2/2001 | Bragulla | A23C 7/02 |
| | | | | 510/498 |
| 6,610,248 | B1 * | 8/2003 | Lichtenberg | A01N 33/04 |
| | | | | 210/764 |
| 11,718,813 | B2 * | 8/2023 | Anderson | A61L 2/18 |
| | | | | 510/383 |
| 2006/0247150 | A1 | 11/2006 | Molinaro et al. | |
| 2006/0257498 | A1 | 11/2006 | Stingl et al. | |
| 2011/0117032 | A1 | 5/2011 | Gilding | |
| 2011/0207649 | A1 * | 8/2011 | Molinaro | C11D 3/30 |
| | | | | 510/382 |
| 2012/0172404 | A1 | 7/2012 | Beilfuss et al. | |
| 2012/0189603 | A1 | 7/2012 | Beilfuss et al. | |
| 2013/0042887 | A1 | 2/2013 | Avery et al. | |
| 2014/0274854 | A1 | 9/2014 | Ortmann et al. | |
| 2018/0007895 | A1 | 1/2018 | Karandikar et al. | |
| 2018/0208875 | A1 | 7/2018 | Man et al. | |

FOREIGN PATENT DOCUMENTS

| | | | | |
|---|---|---|---|---|
| EP | | 0333143 | A3 | 9/1989 |
| EP | | 3015538 | A1 | 5/2016 |
| EP | | 3542628 | A1 | 9/2019 |
| JP | | S4748660 | B | 12/1972 |
| JP | | S61296097 | A | 12/1986 |
| JP | | 2016183242 | A | 10/2016 |
| JP | | 2019182905 | A | 10/2019 |
| WO | | 03099006 | A1 | 12/2003 |
| WO | | 2010069898 | A1 | 6/2010 |
| WO | | 2013061082 | A1 | 5/2013 |
| WO | | 2013098547 | A1 | 7/2013 |
| WO | | 2015070117 | A1 | 5/2015 |
| WO | | 2017049088 | A1 | 3/2017 |
| WO | WO 2017/049088 | | * 3/2017 | .......... C07C 211/13 |

OTHER PUBLICATIONS

Trinetta et al., "Efficacy of an Enzyme-based floor Cleaner Containing N, N-bis (3-aminopropy) laurylamine against foodborne Pathogens on four flooring Types Used in foodservice Environments", Food Protection Trends, vol. 35, No. 2, pp. 106-112, 2015.
International Searching Authority in connection with PCT/US2021/023571 filed Mar. 23, 2021, "The International Search Report and the Written Opinion of the International Searching Authority, Or the Declaration", 15 pages, mailed Aug. 9, 2021.
Mondin et al., "Characterization and quantification of N-(3-aminopropyl)-N-dodecyl-1, 3-propanediamine biocide by NMR, HPLC/MS and titration techniques", Chemosphere, vol. 95, pp. 379-386, 2014.
Seifert et al., "Inhibiting Effect of Surfactants and Heavy Metal Ions on the Denitrification Process", Polish Journal of Environmental Studies, vol. 14, No. 1, pp. 87-93, https://www.researchgate.net/publication/228486080, 2005.
Zorila et al., "Atomic force microscopy study of morphological modifications induced by different decontamination treatments on *Escherichia coli*", Ultramicroscopy, vol. 182, pp. 226-232, 2017.

* cited by examiner

2-IN-1 SANITIZING AND RINSE AID COMPOSITIONS EMPLOYING AMINE BASED SURFACTANTS IN MACHINE WAREWASHING

CROSS REFERENCE TO RELATED APPLICATION

This is a Continuation application of U.S. Ser. No. 17/301,039, filed Mar. 23, 2021, now U.S. Pat. No. 11,718,813, issued Aug. 8, 2023, which claims priority under 35 U.S.C. § 119 to Provisional Application U.S. Ser. No. 62/993,172, filed on Mar. 23, 2020, which is herein incorporated by reference in its entirety including without limitation, the specification, claims, and abstract, as well as any figures, tables, or examples thereof.

TECHNICAL FIELD

Embodiments herein relate generally to the field of warewash sanitizing and rinse aids and methods of employing the same. In particular, the sanitizing and rinse aid compositions disclosed herein have excellent antimicrobial activity and may be employed as a 2-in-1 sanitizing rinse aid with surface activity and enzyme compatibility. Methods of employing the sanitizing and rinse aid compositions are also disclosed.

BACKGROUND

Antimicrobial agents are chemical compositions that are used to prevent microbiological contamination and deterioration of products, materials, and systems. Antimicrobial agents and compositions are used, for example, as disinfectants or sanitizers in association with hard surface cleaning, food preparation, animal feed, cooling water, hospitality services, hospital and medical uses, and pulp and paper manufacturing, and cleaning textiles. Of the diverse categories of antimicrobial agents and compositions, quaternary ammonium compounds represent one of the largest of the classes of agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. It is desirable to boost the antimicrobial activity of such chemicals for us in various applications.

Mechanical warewashing machines including dishwashers have been common in the institutional and household environments for many years. Such automatic warewashing machines clean dishes using two or more cycles which can include initially a wash cycle followed by a rinse cycle. Such automatic warewashing machines can also utilize other cycles, for example, a soak cycle, a pre-wash cycle, a scrape cycle, additional wash cycles, additional rinse cycles, a sanitizing cycle, and/or a drying cycle. Any of these cycles can be repeated, if desired and additional cycles can be used. Rinse aids are conventionally used in warewashing applications to promote drying and to prevent the formation of spots on the ware being washed.

In order to reduce the formation of spotting, rinse agents have commonly been added to water to form an aqueous rinse that is sprayed on the dishware after cleaning is complete. The precise mechanism through which rinse agents work is not established. One theory holds that the surfactant in the rinse agent is absorbed on the surface at temperatures at or above its cloud point, and thereby reduces the solid-liquid interfacial energy and contact angle. This leads to the formation of a continuous sheet which drains evenly from the surface and minimizes the formation of spots. Generally, high foaming surfactants have cloud points above the temperature of the rinse water, and, according to this theory, would not promote sheet formation, thereby resulting in spots. Moreover, high foaming materials are known to interfere with the operation of warewashing machines.

In addition to detergents and sanitizers, rinse aids are also conventionally used in warewashing applications to promote drying and to prevent the formation of spots on the ware being washed. In order to reduce the formation of spotting, rinse aids have commonly been added to water to form an aqueous rinse that is sprayed on the ware after cleaning is complete. A number of rinse aids are currently known, each having certain advantages and disadvantages, such as those disclosed in U.S. Pat. Nos. 3,592,774, 3,625,901, 3,941,713, 4,005,024, 4,187,121, 4,147,559, 4,624,713. In addition, further disclosure of rinse additives including nonionic surfactants is disclosed in Schick, "Nonionic Surfactants", published by Marcel Dekker, and John L. Wilson, Soap and Chemical Specialties, February 1958, pp. 48-52 and 170-171, which is herein incorporated by reference in its entirety.

There remains an ongoing need for alternative and improved rinse aid compositions. There further remains an ongoing need for improved efficacy of dishmachines, including maximizing the efficacy of the combination of detergents, sanitizers and/or rinse aids formulations. Current sanitizing rinse aids generally employ chlorine, oxidizers, and quaternary ammonium chloride compounds. These compounds may reduce a composition's beneficial properties, for example by being corrosive or not being compatible with enzymes due to their oxidizing ability.

Accordingly, it is a feature of the disclosure to develop concentrated and use liquid compositions as well as solid compositions and methods of using the same for warewashing applications to provide desired a sanitizing rinse aid employing an amine-based surfactant, which are not known to be used as sanitizing agents in a machine ware washing application.

It is a further feature of the disclosure to provide a sanitizing rinse aid employing an amine surfactant compound effective at low temperature warewashing applications.

A further feature of the disclosure is to provide a sanitizing rinse aid that is free of chlorine, oxidizers, and quaternary ammonium chloride.

Other embodiments, advantages and features of the present disclosure will become apparent from the following specification taken in conjunction with the accompanying drawings.

SUMMARY

An advantage of the disclosure is the concept that amine-based surfactants can perform as a sanitizing agent in ware washing applications as a part of a cleaning composition or a rinse aid. Beneficially, the sanitizing composition is suitable for use in both low and high temperature warewashing applications, including institutional machine sanitizing. A sanitizing amine surfactant compound based formula is particularly well suited for low temperature and low foam applications including for example, auto-dish rinse aid and sanitizer combination product, or a 2-in-1 sanitizing rinse.

In some embodiments, compositions and methods of making the same provide a sanitizing cleaning/rinse composition containing an amine surfactant with sanitizing activity. In an aspect, the sanitizing rinse/cleaning composition is provided including an amine surfactant having the general formula:

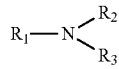

wherein groups $R_1$ is a linear or branched, saturated or unsaturated $C_6$-$C_{18}$ alkyl group or H, and $R_2$ and $R_3$ are selected from the group of H, $(CH_2)_3NH_2$, $(CH_2)_3NHCH_2COOH$, $CH_2COOH$, $(CH_2)_3N(CH_2COOH)_2$, $(CH_2)_3NH_2$. In an aspect, the sanitizing rinse composition is provided as a use solution pH of 1-13, a pH between about 5 and about 13, or a pH between about 7 and about 12, or a pH between about 7 and about 9. In an aspect, the sanitizing rinse composition is substantially free of other sanitizing compounds, such as chlorine, oxidizers, and quaternary ammonium chloride and acts as a non-oxidizing sanitizer.

In an embodiment, the present disclosure provides a 2-in-1 sanitizing rinse composition. In a further embodiment, the present disclosure provides methods of employing the 2-in-1 sanitizing rinse composition. Methods of rinsing a surface or target and providing sanitizing antimicrobial efficacy is provided wherein the method includes applying to a substrate an amine surfactant composition as disclosed according to the various embodiments. In an aspect, the combination provides at least 5 log kill.

Further embodiments also may include a nonionic surfactant as a foam suppressant or defoaming agent in combination with the sanitizing surfactant.

Methods of making the composition are also contemplated.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
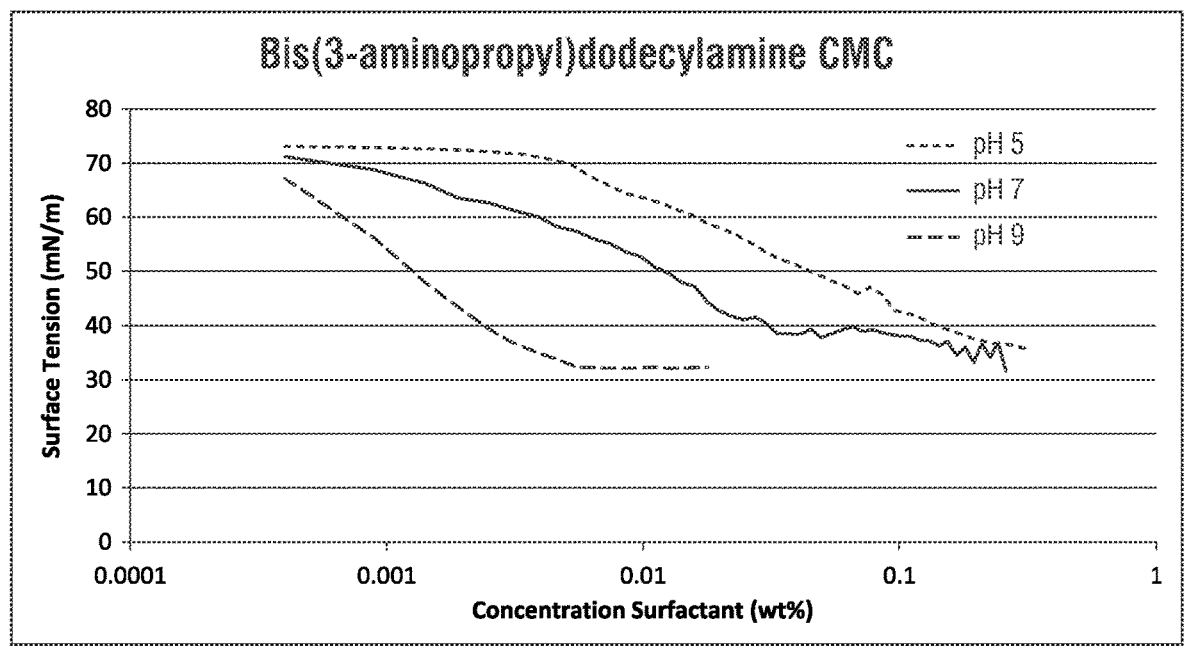
FIG. 1 is a graphical representation of the critical micelle plots of the amine surfactant bis(3-aminopropyl) dodecylamine showing a pH dependent response with respect to CMC likely due to, as the pH shifts from alkaline pH 9, to neutral pH 7, and finally pH 5, the amine based surfactant is becoming more cationic (protonated) in nature resulting in higher electrostatic repulsion, and raising the CMC by an order of magnitude.

Various embodiments of the detergent compositions and their methods of use will be described in detail with reference to the figures. Reference to various embodiments does not limit the scope of the disclosures. Figures represented herein are not limitations to the various embodiments and are presented for exemplary illustration of the detergent compositions disclosed herein.

DETAILED DESCRIPTION

The embodiments of this disclosure are not limited to particular compositions, methods of making and/or methods of employing the same for rinsing and other applications, which can vary and are understood by skilled artisans. So that the disclosure may be more readily understood, certain terms are first defined. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

Definitions

So that the detergent compositions disclosed herein and use thereof may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this disclosure will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms. According to embodiments of the disclosure, a sanitizing rinse provides a 99.999% reduction (5-log order reduction) of the desired organisms (including bacterial contaminants) at a use temperature. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition.

As used herein, the term "substantially free", "free", "free from", "substantially free of", or "free of" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%, less than 0.001% wt-%, less than 0.0001% wt-%, or less than 0.00001 wt-%.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

An "antiredeposition agent" refers to a compound that helps keep soils suspended in water instead of redepositing onto the object being cleaned. Antiredeposition agents are useful in the present disclosure to assist in reducing redepositing of the removed soil onto the surface being cleaned.

The term "threshold agent" refers to a compound that inhibits crystallization of water hardness ions from solution, but that need not form a specific complex with the water hardness ion. Threshold agents suitable for various cleaning applications include but are not limited to a polycarboxylic acid polymers, polyacrylate, a polymethacrylate, an olefin/maleic copolymer, and the like.

As used herein, the term "polymer" generally includes, but is not limited to, homopolymers, copolymers, such as for example, block, graft, random and alternating copolymers, terpolymers, and higher "x" mers, further including their derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

The term "surfactant" as used herein is a compound that contains a lipophilic segment and a hydrophilic segment, which when added to water or solvents, reduces the surface tension of the system.

As used herein, the term "ware" generally refers to items such as eating and cooking utensils, dishes, and other hard surfaces. Ware also refers to items made of various substrates, including glass, ceramic, china, crystal, metal, plastic or natural substances such as, but not limited to clay, bamboo, hemp and the like. Types of plastics that can be cleaned with the compositions according to the disclosure include but are not limited to, those that include polypropylene (PP), high density polyethylene (HDPE), low density polyethylene (LDPE), polyvinyl chloride (PVC), styrene acrylonitrile (SAN), polycarbonate (PC), melamine formaldehyde resins or melamine resin (melamine), acrilonitrile-butadiene-styrene (ABS), and polysulfone (PS). Other exemplary plastics that can be cleaned using the detergent compositions disclosed herein include polyethylene terephthalate (PET) polystyrene polyamide. As used herein, the term "warewashing" refers to washing, cleaning, or rinsing ware.

As used herein, the term "soil" refers to polar or non-polar organic or inorganic substances including, but not limited to carbohydrates, proteins, fats, oils and the like. These substances may be present in their organic state or complexed to a metal to form an inorganic complex.

As used herein, the term "stain" refers to a polar or non-polar substance which may or may not contain particulate matter such as metal oxides, metal hydroxides, metal oxide-hydroxides, clays, sand, dust, natural matter, carbon black, graphite and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the present disclosure as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Sanitizing Cleaning or 2-In-1 Sanitizing Rinse Compositions

The present disclosure relates to dish washing compositions and/or rinse aid compositions with at least one sanitizing amine surfactant and may also include a nonionic surfactant. Exemplary ranges of the rinse compositions are shown in Tables 1A-1C in weight percentage of the detergent compositions.

TABLE 1A

Concentrate liquid compositions.

| Material | First Exemplary Range wt-% | Second Exemplary Range wt-% | Third Exemplary Range wt-% |
|---|---|---|---|
| Amine surfactant | 0.001-95 | 0.01-75 | 0.01-50 |
| Defoaming surfactant | 0.001-50 | 0.01-35 | 0.01-25 |
| Additional functional ingredients | 0-80 | 0-35 | 0-15 |

TABLE 1B

Concentrated liquid compositions with an alcohol alkoxylate and/or an optional builder and/or enzyme.

| Material | First Exemplary Range wt-% | Second Exemplary Range wt-% | Third Exemplary Range wt-% |
|---|---|---|---|
| Amine surfactant | 0.001-95 | 0.01-75 | 0.1-50 |
| Defoaming surfactant | 0.001-50 | 0.01-35 | 0.5-25 |
| Alcohol Alkoxylate | 0.001-50 | 0.01-35 | 0.1-25 |
| Builder | 0-90 | 0-50 | 0-15 |
| Enzyme | 0-30 | 0-20 | 0-15 |
| Additional functional ingredients | 0-80 | 0-35 | 0-15 |
| Water | to 100 | to 100 | to 100 |

TABLE 1C

Concentrated solid compositions with optional builders and/or enzymes.

| Material | First Exemplary Range wt-% | Second Exemplary Range wt-% | Third Exemplary Range wt-% |
|---|---|---|---|
| Amine surfactant | 0.001-95 | 0.01-75 | 0.01-50 |
| Defoaming surfactant | 0.001-50 | 0.01-35 | 0.01-25 |
| Solidifying agents | 1-90 | 5-80 | 10-80 |
| Builder | 0-30 | 0-20 | 0-15 |
| Enzyme | 0-30 | 0-20 | 0-15 |
| Additional functional ingredients | 0-80 | 0-35 | 0-15 |

The sanitizing cleaning or rinse aid compositions may include concentrate solids and/or liquid compositions or may be diluted to form use compositions, as well as ready-to-use compositions. In general, a concentrate refers to a composition that is intended to be diluted with water to provide a use solution that contacts an object to provide the desired cleaning, rinsing, or the like. The cleaning/rinse aid composition that contacts the articles or wares to be washed can be referred to as a concentrate or a use composition (or use solution) dependent upon the formulation employed in methods. It should be understood that the concentration of the sanitizing amine surfactant and other components will vary depending on whether the cleaning composition is provided as a concentrate or as a use solution.

A use solution may be prepared from the concentrate by diluting the concentrate with a solvent, such as water, at a dilution ratio that provides a use solution having the desired detersive properties. The water that is used to dilute the concentrate to form the use composition can be referred to as water of dilution or a diluent and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water. In some embodiments the composition is used in its concentrated form.

In an aspect, a use solution of the cleaning composition has between about 1 ppm to about 5000 ppm amine surfactant and between about 1 ppm to about 5000 ppm defoamer. In a preferred aspect, a use solution of the cleaning composition has between about 10 ppm to about 2000 ppm amine surfactant and between about 1 ppm to about 2000 ppm defoamer. In a preferred aspect, a use solution of the cleaning composition has between about 15 ppm to about 1500 ppm anime surfactant and between about 1 ppm to about 1000 ppm pH defoamer. In a preferred embodiment, the use solution has about 25 ppm or more of an amine surfactant at a pH higher than about 5. In addition, without being limited according to the disclosure, all ranges recited are inclusive of the numbers defining the range and include each integer within the defined range.

The antimicrobial cleaning/rinse aid compositions disclosed herein may be solid concentrate compositions. A "solid" composition refers to a composition in the form of a solid such as a powder, a particle, agglomerate, a flake, a granule, a pellet, a tablet, a lozenge, a puck, a briquette, a brick, a solid block, a unit dose, or another solid form known to those of skill in the art. The term "solid" refers to the state of the cleaning/rinse aid composition under the expected conditions of storage and use of the solid cleaning/rinse aid composition. In general, it is expected that the cleaning/rinse aid composition will remain in solid form when exposed to elevated temperatures of 100° F., 112° F., and preferably 120° F. A cast, pressed, or extruded "solid" may take any form including a block. When referring to a cast, pressed, or extruded solid it is meant that the hardened composition will not flow perceptibly and will substantially retain its shape under moderate stress, pressure, or mere gravity. For example, the shape of a mold when removed from the mold, the shape of an article as formed upon extrusion from an extruder, and the like. The degree of hardness of the solid cast composition can range from that of a fused solid block, which is relatively dense and hard similar to concrete, to a consistency characterized as being malleable and sponge-like, similar to caulking material.

The cleaning/rinse aid compositions disclosed herein can be made available as concentrates that are diluted (or as multiple concentrates that are diluted and combined) prior to or at the point of use to provide a use solution for applications on a variety of surfaces, namely hard surfaces. An advantage of providing concentrates that are later combined or diluted is that shipping and storage costs can be reduced because it can be less expensive to ship and store a concentrate rather than a use solution and is also more sustainable because less packaging is used.

The phrases "cleaning/rinse aid composition" and "sanitizing cleaning/rinse aid composition" refer to the cleaning/rinse aid composition provided as a concentrate or as a use composition according to the disclosure, which may be provided in a variety of formulations, including for example liquid, solid, powder, paste or gel. The term "concentrate" refers to a relatively concentrated form of the cleaning/rinse aid composition that can be diluted with a diluent to form a use composition. An exemplary diluent that can be used to dilute the concentrate to form the use composition is water. In general, the use composition refers to the composition that contacts an article to provide a desired action. For example, a warewashing cleaning/rinse aid composition that is provided as a use composition can contact ware for cleaning the ware. In addition, the concentrate or the diluted concentrate can be provided as the use composition. For example, the concentrate can be referred to as the use composition when it is applied to an article without dilution. In many situations, it is expected that the concentrate will be diluted to provide a use composition that is then applied to an article.

Amine Surfactant

The 2-in-1 sanitizing rinse compositions according to the disclosure include at least one sanitizing amine compound. Certain amines are known to have antimicrobial activity.

Accordingly, various amine-based compounds with antimicrobial activity may be used in the compositions of the disclosure. The term "amine based" generally refers to any compound with the formula:

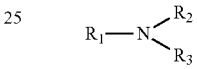

wherein group $R_1$ is a linear or branched, saturated or unsaturated $C_4$-$C_{24}$ alkyl group or H. $R_2$ and $R_3$ may be the same or different and may be, but not limited to, H, $(CH_2)_3NH_2$, $(CH_2)_3NHCH_2COOH$, $CH_2COOH$, and/or $(CH_2)_3N(CH_2COOH)_2$. In some embodiments, $R_1$ is a saturated carbon chain with less than 24 alkyl groups. In other embodiments, $R_1$ is a $C_4$-$C_{18}$ alkyl group, a $C_6$-$C_{18}$ alkyl group, a $C_6$-$C_{14}$ alkyl group, and/or mixtures thereof.

Figure 9:
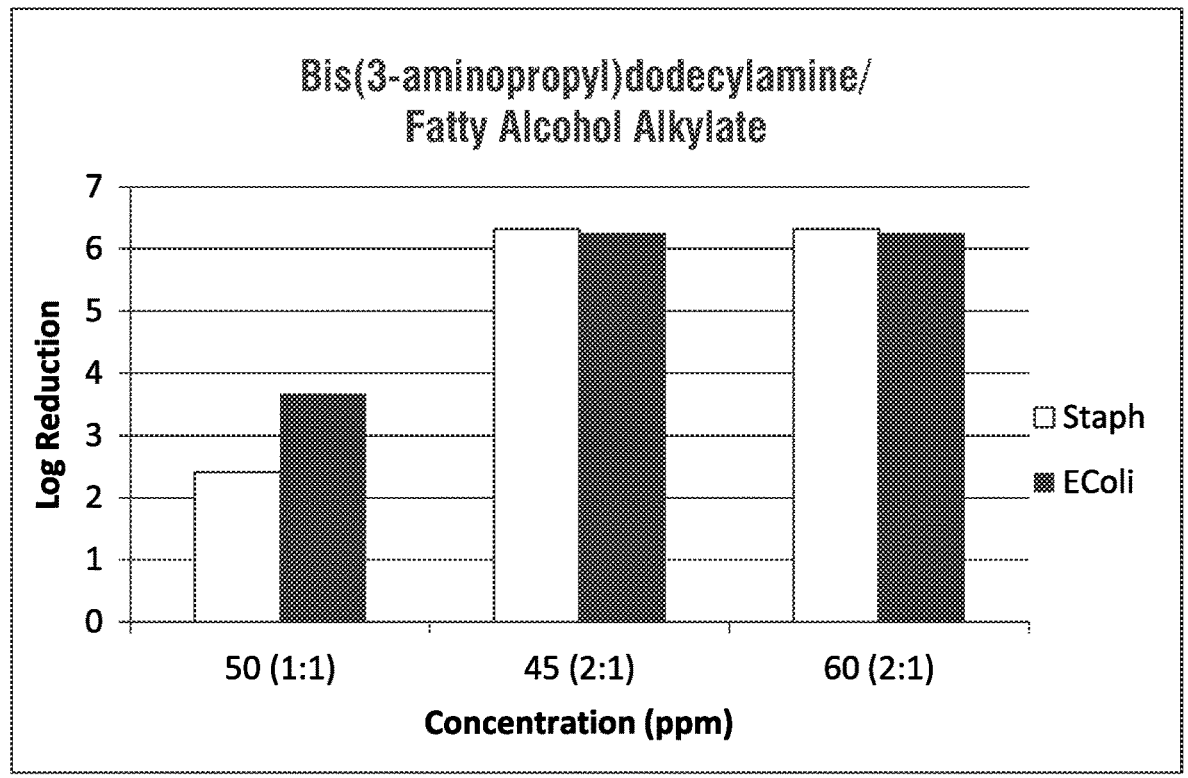
FIG. 9 is a graphical representation showing that the addition of a nonionic surfactant does not impact the sanitizing effect of bis(3-aminopropyl)dodecylamine on Staphylococcus aureus and E. coli.
Figure 10:
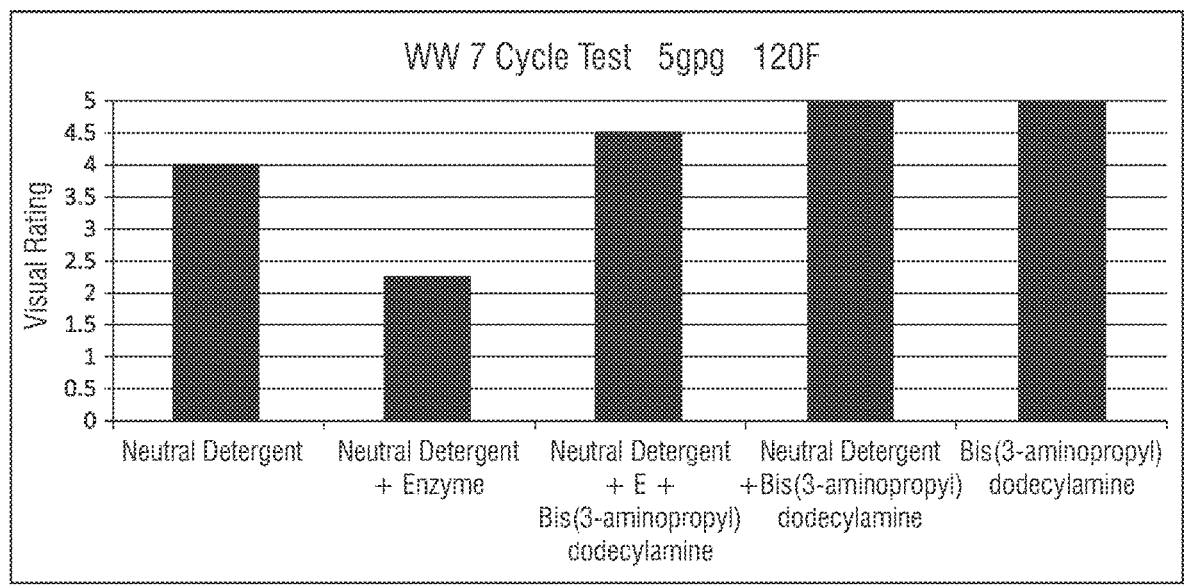
FIG. 10 is a graphical representation showing the results of a protein soil removal test at neutral detergent pH with or without a protease and with or without an amine surfactant. The lower the rating the more detergency achieved.
Figure 11:
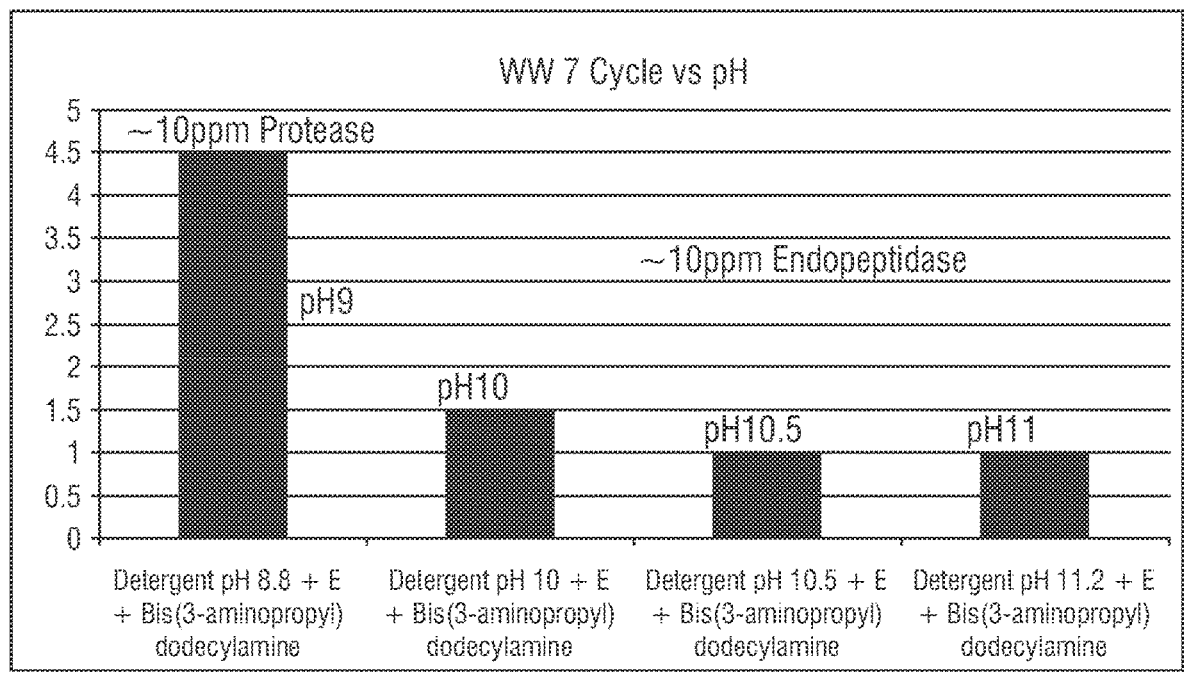
FIG. 11 is a graphical representation showing the results of a protein soil removal test at different basic detergent pHs with either a protease or an endo-peptidase and with an amine surfactant. The lower the rating the more detergency achieved.

The use of these amine based surfactants results in efficiency and provides excellent antimicrobe efficacy (see FIGS. 3-9), rinse aid functionality, low CMC (see FIGS. 1 and 2), they are non-corrosive, have a low odor, and may be compatible with enzymes (see FIGS. 10-11).

In preferred embodiments, the amine-based surfactants include N-alkylaminopropyl glycerin, bis(3-aminopropyl) dodecylamine, N—$C_{10-16}$-alkyltrimethylenediamine reaction products with chloroacetic acid, and/or combinations thereof. By way of example, such as N—$C_{10-16}$-alkyltrimethylenediamines reaction products with chloroacetic acid may be represented by the following structures:

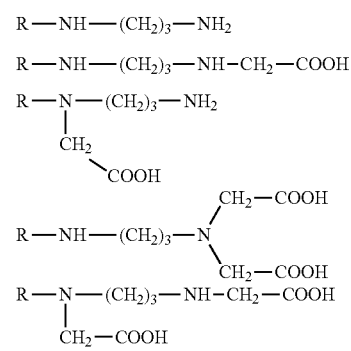

where R is linear or branched, saturated or unsaturated $C_4$-$C_{24}$ alkyl group or H.

In other embodiments, the compositions of the disclosure are free of other antimicrobials, such as chlorine, oxidizers, and quaternary ammonium chloride.

An effective amount of the amine-based surfactant is provided in combination with one or more defoaming agents to provide sanitizing efficacy against a broad spectrum of microbes, including gram negative microbes such as *E. coli* in low temperature dish machines. Suitable concentrations of the amine based surfactant in a use solution include between 1 ppm and about 10,000 ppm, 1 ppm and about 1,000 ppm, 5 ppm and about 400 ppm, 10 ppm and about 400 ppm, 20 ppm and about 400 ppm, 25 ppm and about 400 ppm, 50 ppm and about 400 ppm, 75 ppm and about 400 ppm, or 100 ppm and about 400 ppm. Without being limited according to the disclosure, all ranges recited are inclusive of the numbers defining the range and include each integer within the defined range.

Defoaming Agents

In embodiments of the disclosure, the compositions disclosed herein may include a defoaming agent. In an embodiment, the compositions disclosed herein include a defoaming agent. In a preferred embodiment, the defoaming agent is a nonionic surfactant. In a preferred embodiment, the defoaming agent is a nonionic alkoxylated surfactant. In another preferred embodiment, the defoaming agent is a nonionic surfactant having a formula RO—$(PO)_{0-5}(EO)_{1-30}(PO)_{1-30}$, or RO—$(PO)_{1-30}(EO)_{1-30}(PO)_{1-30}$, wherein R is a $C_{8-18}$ linear or branched alkyl group; EO=ethylene oxide; PO=propylene oxide. Exemplary suitable alkoxylated surfactants include ethylene oxide/propylene block copolymers (EO/PO copolymers); poloxamers; alkoxylated, predominantly unbranched fatty alcohols with higher alkene oxides alongside ethylene oxide; capped EO/PO copolymers; partially capped EO/PO copolymers; fully capped EO/PO copolymers; alcohol alkoxylates; capped alcohol alkoxylates; mixtures thereof, or the like.

Other defoaming agents can include silicone compounds such as silica dispersed in polydimethylsiloxane, polydimethylsiloxane, and functionalized polydimethylsiloxane, dimethicone, fatty amides, hydrocarbon waxes, fatty acids, fatty esters, fatty alcohols, fatty acid soaps, ethoxylates, mineral oils, polyethylene glycol esters, alkyl phosphate esters such as monostearyl phosphate, and the like. A discussion of defoaming agents may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated by reference herein for all purposes.

Nonionic surfactants generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties. According to the disclosure, the nonionic surfactant useful in the composition is a low-foaming nonionic surfactant. Examples of nonionic low foaming surfactants useful in the present disclosure include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are poloxamers and Ethoxylated and propoxylated ethylene diamines. Poloxamers compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from 1,000 to 4,000. Ethylene oxide is then added to sandwich this hydrophobe between hydrophilic groups, controlled by length to constitute from about 10% by weight to about 80% by weight of the final molecule. Ethoxylated and propoxylated ethylene diamines compounds are tetrafunctional block copolymers derived from the sequential addition of propylene oxide and ethylene oxide to ethylenediamine. The molecular weight of the propylene oxide hydrotype ranges from 500 to 7,000; and, the hydrophile, ethylene oxide, is added to constitute from 10% by weight to 80% by weight of the molecule.

2. Condensation products of one mole of alkyl phenol wherein the alkyl chain, of straight chain or branched chain configuration, or of single or dual alkyl constituent, contains from 8 to 18 carbon atoms with from 3 to 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples include branched polyoxyethylene nonylphenylether and alkyl phenol ethoxylate.

3. Condensation products of one mole of a saturated or unsaturated, straight or branched chain alcohol having from 6 to 24 carbon atoms with from 3 to 50 moles of ethylene oxide. The alcohol moiety can consist of mixtures of alcohols in the above delineated carbon range or it can consist of an alcohol having a specific number of carbon atoms within this range.

4. Condensation products of one mole of saturated or unsaturated, straight or branched chain carboxylic acid having from 8 to 18 carbon atoms with from 6 to 50 moles of ethylene oxide. The acid moiety can consist of mixtures of acids in the above defined carbon atoms range or it can consist of an acid having a specific number of carbon atoms within the range. Examples include 2-hydroxyethyl dodecanoate, PEG 100 stearate, and PEG-150 disterate.

5. Compounds with the following structure: RO—$(PO)_{0-5}(EO)_{1-30}(PO)_{1-30}$, wherein R is a C8-18 linear or branched alkyl group; EO=ethylene oxide; PO=propylene oxide.

6. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from 1,000 to 3,100 with the central hydrophile including 10% by weight to 80% by weight of the final molecule.

7. Alkoxylated diamines produced by the sequential addition of propylene oxide and ethylene oxide to ethylenediamine. The hydrophobic portion of the molecule weighs from 250 to 6,700 with the central hydrophile including 0.1% by weight to 50% by weight of the final molecule.
8. Alkoxylated diamines produced by the sequential addition of ethylene oxide and propylene oxide to ethylenediamine. The hydrophobic portion of the molecule weighs from 250 to 6,700 with the central hydrophile including 0.1% by weight to 50% by weight of the final molecule.
9. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and short chain fatty acids, alcohols or alkyl halides containing from 1 to 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.
10. Polyoxyalkylene surface-active agents which are advantageously used in the compositions of this disclosure correspond to the formula: $P[(C_3H_6)_n(C_2H_4O)_m H]_x$ wherein P is the residue of an organic compound having from 8 to 18 carbon atoms and containing x reactive hydrogen atoms in which x has a value of 1 or 2, n has a value such that the molecular weight of the polyoxyethylene portion is at least 44 and m has a value such that the oxypropylene content of the molecule is from 10% to 90% by weight. In either case the oxypropylene chains may contain optionally, but advantageously, small amounts of ethylene oxide and the oxyethylene chains may contain also optionally, but advantageously, small amounts of propylene oxide.
11. Alkoxylated amines or, most particularly, alcohol alkoxylated/aminated/alkoxylated surfactants. These non-ionic surfactants may be at least in part represented by the general formulae:

$R^{20}—(PO)_s N-(EO)_t H$, $R_2 0-(PO)_s N-(EO)_t H(EO)_t H$, and $R^{20}—N(EO)_t H$;

in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula:

$R^{20}—(PO)_v—N[(EO)_w H][(EO)_z H]$ in which $R^{20}$ is as defined above, v is 1 to 20 (e.g., 1, 2, 3, or 4 (preferably 2)), and w and z are independently 1-10, preferably 2-5.

In an embodiment, the claimed compositions include from about 0.001 wt % to about 50 wt %, from about 0.01 wt % to about 35 wt %, from about 0.01 wt % to about 25 wt %, or from about 0.5 wt % to about 25 wt % of one or more defoaming surfactants. In addition, without being limited according to the detergent compositions disclosed herein, all ranges recited are inclusive of the numbers defining the range and include each integer within the defined range.

Additional Optional Ingredients

The components of the compositions can further be combined with various functional components. In some embodiments, the compositions including the amine surfactants and defoaming agents make up a large amount, or even substantially all of the total weight of the composition. For example, in some embodiments few or no additional functional ingredients are disposed therein. In other embodiments, additional functional ingredients may be included in the compositions. The functional ingredients provide desired properties and functionalities to the compositions. For the purpose of this application, the term "functional ingredient" includes a material that when dispersed or dissolved in the aqueous use solution provides a beneficial property in a particular use.

Some particular examples of functional materials are discussed in more detail below, although the particular materials discussed are given by way of example only, and that a broad variety of other functional ingredients may be used.

In some embodiments, the compositions may include additional functional ingredients including, for example, additional surfactants, including enzymes, nonionic surfactants, thickeners and/or viscosity modifiers, solvents, solubility modifiers, humectants, metal protecting agents, stabilizing agents, corrosion inhibitors, sequestrants and/or chelating agents, solidifying agent, sheeting agents, pH modifying components, including alkalinity and/or acidity sources, aesthetic enhancing agents (i.e., colorants, odorants, or perfumes), other cleaning agents, hydrotropes or couplers, buffers, and the like.

In some embodiments, the compositions of the disclosure do not include nonionic surfactants, providing a benefit of a sanitizing rinse aid employing the amine surfactant and defoaming agent, without the inclusion of a nonionic surfactant for wetting, sheeting and/or rinsing characteristics. Instead, the benefit of the disclosure is the surface activity as a result of the biocidal agent employed, namely the amine surfactant and defoaming agent. Additionally, the compositions can be used in conjunction with one or more conventional cleaning agents, e.g., an alkaline detergent.

Enzymes

In some embodiments, the compositions of the present disclosure include an enzyme. Preferred enzymes include proteases, amylases, cellulases, lipases, and combinations of the same. More preferred enzymes are proteases. The enzyme is preferably in an amount between about 0 wt. % to about 30 wt. %, from about 0 wt. % to about 20 wt. %, or from about 0 wt. % to about 15 wt. %.

Proteases

Any protease or mixture of proteases, from any source, can be used in the enzymatic detergent compositions, provided that the selected enzyme is stable in the desired pH range (between about 6 and about 9). For example, the protease enzymes can be derived from a plant, an animal, or a microorganism such as a yeast, a mold, or a bacterium. Preferred protease enzymes include, but are not limited to, the enzymes derived from *Bacillus subtilis, Bacillus lentus, Bacillus licheniformis* and *Streptomyces griseus*. Protease enzymes derived from *B. subtilis* are most preferred. The protease can be purified or a component of a microbial extract, and either wild type or variant (either chemical or recombinant). Exemplary proteases include subtilisins, a serine endopeptidase, E.C. 3.4.21.

Amylases

Any amylase or mixture of amylases (E.C. 3.2.1.1), from any source, can be used in the enzymatic detergent compositions, provided that the selected enzyme is stable in the desired pH range (between about 6 and about 9). For example, the amylase enzymes can be derived from a plant, an animal, or a microorganism such as a yeast, a mold, or a bacterium. Preferred amylase enzymes include, but are not limited to, those derived from a *Bacillus*, such as *B. licheniformis, B. amyloliquefaciens, B. subtilis,* or *B. stearothermophilus*. Amylase enzymes derived from *B. subtilis* are most preferred. The amylase can be purified or a component of a microbial extract, and either wild type or variant (either chemical or recombinant).

Cellulases

Any cellulase or mixture of cellulases (E.C. 3.2.1.4), from any source, can be used in the enzymatic detergent compositions, provided that the selected enzyme is stable in the desired pH range (between about 6 and about 9). For example, the cellulase enzymes can be derived from a plant, an animal, or a microorganism such as a fungus or a bacterium. Preferred cellulase enzymes include, but are not limited to, those derived from *Humicola insolens, Humicola* strain DSM1800, or a cellulase 212-producing fungus belonging to the genus *Aeromonas* and those extracted from the hepatopancreas of a marine mollusk, *Dolabella auricula solander*. The cellulase can be purified or a component of a microbial extract, and either wild type or variant (either chemical or recombinant).

Lipases

Any lipase or mixture of lipases (E.C. 3.1.1), from any source, can be used in the enzymatic detergent compositions, provided that the selected enzyme is stable in the desired pH range (between about 6 and about 9). For example, the lipase enzymes can be derived from a plant, an animal, or a microorganism such as a fungus or a bacterium. Preferred protease enzymes include, but are not limited to, the enzymes derived from a *Pseudomonas*, such as *Pseudomonas stutzeri* ATCC 19.154, or from a *Humicola*, such as *Humicola lanuginosa* (typically produced recombinantly in *Aspergillus oryzae*). The lipase can be purified or a component of a microbial extract, and either wild type or variant (either chemical or recombinant).

Other Enzymes

The enzymatic detergent compositions can comprise additional enzymes in addition to the foregoing. Additional suitable enzymes can include, but are not limited to, cutinases, peroxidases, gluconases, or mixtures thereof.

Alkalinity and/or Acidity Source

In some embodiments, the compositions of the present disclosure include an alkalinity source and/or acidulant. In a preferred embodiment, the compositions of the present disclosure include an acidulant. The acidulant can be effective to form a concentrate composition or a use solution with a desired acidic to neutral pH. The acidulant can be effective to form a use composition with pH of about 7, about 6 or less, about 5 or less.

In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, benzene sulfonic acid, formic acid, acetic acid, mono, di, or tri-carboxylic acids (succinic, citric), picolinic acid, dipicolinic acid, and mixtures thereof. In some embodiments, the compositions of the present disclosure are free or substantially free of a phosphorous based acid. In some embodiments, acidulant selected can also function as a stabilizing agent. Thus, the compositions of the present disclosure can be substantially free of an additional stabilizing agent.

According to some embodiments, the detergent compositions include an alkalinity source. Exemplary alkalinity sources include alkali metal carbonates and/or alkali metal hydroxides. In various aspects, a combination of both alkali metal carbonates and/or alkali metal hydroxides are employed as the alkalinity source. The alkalinity source can be effective to form a use composition with pH of about 7, about 8 or more, about 9 or more, about 9, about 10 or more, about 10, about 11 or more, about 12 or more, about 13, or the like.

Alkali metal carbonates used in the formulation of detergents are often referred to as ash-based detergents and most often employ sodium carbonate. Additional alkali metal carbonates include, for example, sodium or potassium carbonate. In another embodiments, the alkali metal carbonates, and alkali metal hydroxides are further understood to include bicarbonates and sesquicarbonates. According to the detergent compositions disclosed herein, any "ash-based" or "alkali metal carbonate" shall also be understood to include all alkali metal carbonates, bicarbonates and/or sesquicarbonates.

Alkali metal hydroxides used in the formulation of detergents are often referred to as caustic detergents. Examples of suitable alkali metal hydroxides include sodium hydroxide, potassium hydroxide, and lithium hydroxide. Exemplary alkali metal salts include sodium carbonate, potassium carbonate, and mixtures thereof. The alkali metal hydroxides may be added to the composition in any form known in the art, including as solid beads, dissolved in an aqueous solution, or a combination thereof. Alkali metal hydroxides are commercially available as a solid in the form of prilled solids or beads having a mix of particle sizes ranging from about 12-100 U.S. mesh, or as an aqueous solution, as for example, as a 45% and a 50% by weight solution.

In addition to the first alkalinity source, the detergent composition may comprise a secondary alkalinity source. Examples of useful secondary alkaline sources include, but are not limited to, alkali metal silicates such as sodium or potassium silicate or metasilicate; alkali metal carbonates such as sodium or potassium carbonate, bicarbonate, sesquicarbonate; alkali metal borates such as sodium or potassium borate; and ethanolamines and amines. Such alkalinity agents are commonly available in either aqueous or powdered form, either of which is useful in formulating the present detergent compositions.

An effective amount of one or more acidulant and/or alkalinity sources is provided in the detergent composition. An effective amount is referred to herein as an amount that provides a use composition having a pH of at least about 5, preferably at least about 7, at least about 9, and at most 13. The use solution pH range is preferably between about 1 and about 13, about 5 and about 13, and more preferably between about 7 to 9. In addition, without being limited according to the detergent compositions disclosed herein, all ranges recited are inclusive of the numbers defining the range and include each integer within the defined range.

Stabilizing Agents

In some embodiments, the compositions of the present disclosure include one or more stabilizing agents. In some embodiments, an acidic stabilizing agent can be used. Thus, in some embodiments, the compositions of the present disclosure can be substantially free of an additional acidulant. Suitable stabilizing agents include, for example, chelating agents or sequestrants. Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2, 6-dicarboxylic acid (dipicolinic acid).

In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g, HEDP are included in the compositions of the present disclosure. Specific examples include, but are not limited to, 1-hydroxyethylidene-1, 1-diphosphonic acid, amino(tri(methylenephosphonic acid)), (N[CH$_2$PO$_3$H$_2$]$_3$), ethylenediamine[tetra(methylenephosphonic acid)], and 2-phosphonobutane-1,2,4-tricarboxylic acid.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and Alanine-N, N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0 to about 10 wt-% stabilizing agent, about 0.01 to about 10 wt-% stabilizing agent, about 0.4 to about 4 wt-% stabilizing agent, about 0.6 to about 3 wt-% stabilizing agent, about 1 to about 2 wt-% stabilizing agent. It is to be understood that all values and ranges within these values and ranges are encompassed by the present disclosure.

Wetting Agents

Also useful in the compositions of the disclosure are wetting agents. Wetting agents function to increase the surface contact or penetration activity of the antimicrobial composition of the disclosure. Wetting agents which can be used in the composition of the disclosure include any of those constituents known within the art to raise the surface activity of the composition of the disclosure. In aspects of the disclosure various amine surfactants are suitable for the cleaning/rinse aid and sanitizing cleaning/rinse aid application without the use of further wetting agents in the formulation. Wetting agents can be present at a concentration range from about 0.01 wt-% to 20 wt-%, 0.01 wt-% to 20 wt-%, from about 0.01 wt-% to 5 wt-%, or from about 0.01 wt-% to about 1 wt-%.

Thickening or Gelling Agents

The compositions of the present disclosure can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity of thickener within the present composition ranges from about 0.1 wt-% to about 5 wt-%, from about 0.1 wt-% to about 1.0 wt-%, or from about 0.1 wt-% to about 0.5 wt-%.

Additional Surfactants

The sanitizing rinse compositions according to the disclosure may include additional surfactants. In a particular aspect, nonionic surfactants are particularly useful for applications of use requiring additional defoaming. In an aspect, it is beneficial the sanitizing and rinse compositions do not require formulation with the nonionic surfactant for low-foaming surface activity. However, in some aspects, a nonionic surfactant may be desired in combination with the compositions of the disclosure (such as included in a detergent formulation employed in combination therewith). For example, in certain embodiments, such as food soil defoaming applications, a nonionic surfactant may be desirable to preferably include alcohol alkoxylates and EO/PO block copolymers.

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties. Useful nonionic surfactants include:

Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are poloxamers and ethoxylated and propoxylated ethylene diamines. Poloxamers are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Ethoxylated and propoxylated ethylene diamines compounds are tetra-flinctional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols.

Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this disclosure for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty esters or acylated carbohydrates to compositions of the present disclosure containing amylase and/or lipase enzymes because of potential incompatibility.

Examples of Nonionic Low Foaming Surfactants Include:

Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. Likewise, the ethoxylated and propoxylated ethylene diamines reverse surfactants are produced by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional Examples of Effective Low Foaming Nonionics Include:

The alkylphenoxypolyethoxyalkanols of U.S. Pat. No. 2,903,486 issued Sep. 8, 1959 to Brown et al. and represented by the formula

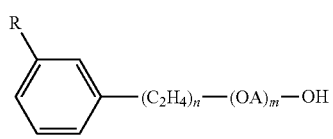

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O_n (C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this disclosure correspond to the formula: $P[(C_3H_6O)_n$ $(C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction, such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or —$(C_2H_4O)_xH$, where x is in the range of from 1 to 3.

A useful class of non-ionic surfactants include the class defined as alkoxylated amines or, most particularly, alcohol alkoxylated/aminated/alkoxylated surfactants. These nonionic surfactants may be at least in part represented by the general formulae: $R^{20}$—$(PO)_sN$-$(EO)_tH$, $R^{20}$—$(PO)_sN$-$(EO)_tH(EO)_tH$, and $R^{20}$—$N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}$—$(PO)_v$—$N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. Preferred nonionic surfactants for the compositions of the disclosure include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present disclosure. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface-active agents are another class of nonionic surfactant useful in compositions of the present disclosure. Generally, semi-polar nonionics are high foamers and foam stabilizers, which can limit their application in CIP systems. However, within compositional embodiments of this disclosure designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

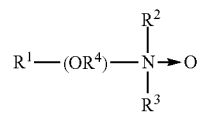

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water-soluble phosphine oxides having the following structure:

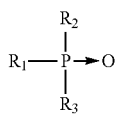

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water-soluble sulfoxide compounds which have the structure:

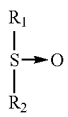

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the disclosure include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present disclosure include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers and reverse block copolymers, alcohol alkoxylates, and capped alcohol alkoxylates, mixtures thereof, or the like.

Sequestrants

The composition can contain an organic or inorganic sequestrant or mixtures of sequestrants. Organic sequestrants such as sodium citrate, the alkali metal salts of nitrilotriacetic acid (NTA), dicarboxymethyl glutamic acid tetrasodium salt (GLDA), EDTA, alkali metal gluconates, polyelectrolytes such as a polyacrylic acid, and the like can be used herein. The most preferred sequestrants are organic sequestrants such as sodium gluconate due to the compatibility of the sequestrant with the formulation base.

The present disclosure can also incorporate sequestrants to include materials such as, complex phosphate sequestrants, including sodium tripolyphosphate, sodium hexametaphosphate, and the like, as well as mixtures thereof. Phosphates, the sodium condensed phosphate hardness sequestering agent component functions as a water softener, a cleaner, and a detergent builder. Alkali metal (M) linear and cyclic condensed phosphates commonly have a $M_2O:P_2O_5$ mole ratio of about 1:1 to 2:1 and greater. Typical polyphosphates of this kind are the preferred sodium tripolyphosphate, sodium hexametaphosphate, sodium metaphosphate as well as corresponding potassium salts of these phosphates and mixtures thereof. The particle size of the phosphate is not critical, and any finely divided or granular commercially available product can be employed.

Solidification Agents or Hardening Agents

If it is desirous to prepare compositions of the disclosure as a solid, a solidification agent may be included into the composition. In some embodiments, the solidification agent can form and/or maintain the composition as a solid cleaning/rinse aid composition. In other embodiments, the solidification agent can solidify the composition without unacceptably detracting from the eventual release of the active ingredients. The solidification agent can include, for example, an organic or inorganic solid compound having a neutral inert character or making a functional, stabilizing or detersive contribution to the present composition. Suitable solidification agents include solid polyethylene glycol (PEG), solid polypropylene glycol, solid EO/PO block copolymer, amide, urea (also known as carbamide), nonionic surfactant (which can be employed with a coupler), anionic surfactant, starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like.

Suitable glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like.

Suitable amide solidification agents include stearic monoethanolamide, lauric diethanolamide, stearic diethanolamide, stearic monoethanol amide, cocodiethylene amide, an alkylamide, mixtures thereof, and the like. In an embodiment, the present composition can include glycol (e.g., PEG) and amide.

Suitable inorganic solidification agents include phosphate salt (e.g., alkali metal phosphate), sulfate salt (e.g., magnesium sulfate, sodium sulfate or sodium bisulfate), acetate salt (e.g., anhydrous sodium acetate), Borates (e.g., sodium borate), Silicates (e.g., the precipitated or fumed forms), carbonate salt (e.g., calcium carbonate or carbonate hydrate), other known hydratable compounds, mixtures thereof, and the like. In an embodiment, the inorganic solidification agent can include organic phosphonate compound and carbonate salt, such as an E-Form composition.

In some embodiments, the compositions of the present disclosure can include any agent or combination of agents that provide a requisite degree of solidification and aqueous solubility can be included in the present compositions. In other embodiments, increasing the concentration of the solidification agent in the present composition can tend to increase the hardness of the composition. In yet other embodiments, decreasing the concentration of solidification agent can tend to loosen or soften the concentrate composition.

In some embodiments, the solidification agent can include any organic or inorganic compound that imparts a solid character to and/or controls the soluble character of the present composition, for example, when placed in an aqueous environment. For example, a solidifying agent can provide controlled dispensing if it has greater aqueous solubility compared to other ingredients in the composition. Urea can be one such solidification agent. By way of further example, for systems that can benefit from less aqueous solubility or a slower rate of dissolution, an organic nonionic or amide hardening agent may be appropriate.

In some embodiments, the compositions of the present disclosure can include a solidification agent that provides for convenient processing or manufacture of the present composition. For example, the solidification agent can be selected to form a composition that can harden to a solid form under ambient temperatures of about 30 to about 50° C. after mixing ceases and the mixture is dispensed from the mixing system, within about 1 minute to about 3 hours, or about 2 minutes to about 2 hours, or about 5 minutes to about 1 hour.

In an exemplary aspect, a solid cleaning/rinse aid may include an effective amount of a solidification agent or a hardening agent, as for example, urea which vary the solubility of the composition in an aqueous medium during use such that the cleaning/rinse aid and/or other active ingredients may be dispensed from the solid composition over an extended period of time. The composition may include a hardening agent in an amount in the range of up to about 50 wt %. In other embodiments, the hardening agent may be present in amount from about 20 wt % to about 40 wt %, or in the range of about 5 to about 15 wt %.

The compositions of the present disclosure can include solidification agent at any effective amount. The amount of solidification agent included in the present composition can vary according to the type of composition, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. Suitable amounts can include about 1 to about 99 wt-%, about 1.5 to about 85 wt-%, about 2 to about 80 wt-%, about 10 to about 45 wt-%, about 15% to about 40 wt-%, about 20% to about 30 wt-%, about 30% to about 70%, about 40% to about 60%, up to about 50 wt-%, about 40% to about 50%.

Use Compositions

The 2-in-1 sanitizing rinse compositions may include concentrate compositions or may be diluted to form use compositions. In general, a concentrate refers to a composition that is intended to be diluted with water to provide a use solution that contacts a surface and/or product in need of treatment to provide the desired rinsing, sanitizing or the like. The 2-in-1 sanitizing rinse compositions that contacts the surface and/or product in need of treatment can be referred to as a concentrate or a use composition (or use solution) dependent upon the formulation employed in methods according to the disclosure. It should be understood that the concentration of the quaternary ammonium compound and anionic surfactants in the composition will vary depending on whether the composition is provided as a concentrate or as a use solution.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent and can vary from one location to another. The typical dilution factor is between about 1 and about 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In preferred embodiments the present disclosure includes concentrate compositions and use compositions. In an embodiment, a concentrate composition can be diluted to a use solution before applying to an object. The concentrate can be provided, and an end user can dilute the concentrate with water or an aqueous diluent to a use solution. The level of active components in the concentrate composition is dependent on the intended dilution factor and the desired activity of the antimicrobial composition. Generally, a dilution of about 1 fluid ounce to about 10 gallons of water to about 10 fluid ounces to about 1 gallon of water is used for aqueous compositions of the present disclosure. In some embodiments, higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, the concentrated compositions can be diluted at a dilution ratio of about 0.05 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent.

In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent.

Amounts of an ingredient in a use composition can be calculated from the amounts listed above for concentrate compositions and these dilution factors. In some embodiments, the concentrated compositions of the present disclosure are diluted such that the quaternary ammonium component is present at from about 10 ppm to about 100 ppm, or about 20 ppm to about 80 ppm. In other embodiments, the concentrated compositions of the present disclosure are diluted such that the amine surfactant component is present at about 20 ppm or more, about 40 ppm or more, about 60 ppm or more, about 80 ppm or more, about 100 ppm or more, about 500 ppm, about 1000 ppm, or about 10,000 to about 20,000 ppm. It is to be understood that all values and ranges between these values and ranges are encompassed by the present disclosure.

Methods of Use

The 2-in-1 sanitizing rinse compositions according to the disclosure beneficially provide synergistic efficacy by formulating compositions comprising amine-based surfactants. In a particular beneficial aspect, the 2-in-1 sanitizing rinse compositions according to the disclosure are free of other chlorine, oxidizers, and/or quaternary ammonium chloride.

In an aspect, the present disclosure beneficially provides a reduced surface tension of the aqueous solutions, or use solution, according to the disclosure. In an aspect, the surface tension is reduced to less than about 70 mN/m, and preferably between about 25 and about 70 mN/m. In another aspect, the surface tension is reduced to less than about 70 mN/m, less than about 60 mN/m, less than about 50 mN/m, less than about 40 mN/m, or less than about 30 mN/m.

In an aspect, the present disclosure includes use of the compositions for sanitizing and rinsing surfaces and/or products. In another aspect, the compositions of the disclosure are particularly suitable for use as a hard surface cleaner and/or sanitizer, food contact sanitizer (including direct or indirect contact sanitizer), tissue contact sanitizer (including for example fruits and vegetables), fast drying sanitizer for various hard surfaces (including for example healthcare surfaces, instruments, food and/or beverage surfaces, processing surfaces, and the like), any-streaking or smearing hard surface sanitizer, and the like. The present methods can be used in the methods, processes or procedures described and/or claimed in U.S. Pat. Nos. 5,200,189, 5,314,687, 5,718,910, 6,165,483, 6,238,685B1, 8,017,409 and 8,236,573, each of which are herein incorporated by reference in their entirety.

The methods of use are particularly suitable for warewashing. Suitable methods for using the sanitizing cleaning/rinse aid compositions for warewashing are set forth in U.S. Pat. No. 5,578,134, which is herein incorporated by reference in its entirety. Beneficially, according to various embodiments of the disclosure, the methods provide the following benefits: retained sanitizing effect with suppressed foam formation.

Exemplary articles in the warewashing industry that can be treated with a sanitizing cleaning/rinse aid composition according to the disclosure include plastics, dishware, cups, glasses, flatware, and cookware. For the purposes of this disclosure, the terms "dish" and "ware" are used in the broadest sense to refer to various types of articles used in the preparation, serving, consumption, and disposal of food stuffs including pots, pans, trays, pitchers, bowls, plates, saucers, cups, glasses, forks, knives, spoons, spatulas, and other glass, metal, ceramic, plastic composite articles commonly available in the institutional or household kitchen or dining room. In general, these types of articles can be referred to as food or beverage contacting articles because they have surfaces which are provided for contacting food and/or beverage. When used in these warewashing applications, the cleaning/rinse aid should provide effective sheeting action and low foaming (or non-foaming) properties. In addition to having the desirable properties described above, it may also be useful for the sanitizing cleaning/rinse aid composition to be biodegradable, environmentally friendly, and generally nontoxic. A cleaning/rinse aid of this type may be described as being "food grade".

The methods of use are suitable for treating a variety of surfaces, products and/or targets in addition to ware. For example, these may include a food item or a plant item and/or at least a portion of a medium, a container, an equipment, a system or a facility for growing, holding, processing, packaging, storing, transporting, preparing, cooking or serving the food item or the plant item. The present methods can be used for treating any suitable plant item. In some embodiments, the plant item is a grain, fruit, vegetable or flower plant item, a living plant item or a harvested plant item. In addition, the present methods can be used for treating any suitable food item, e.g., an animal product, an animal carcass or an egg, a fruit item, a vegetable item, or a grain item. In still other embodiments, the food item may include a fruit, grain and/or vegetable item.

In a still further embodiment, the methods of the disclosure are suitable for meeting various regulatory standards, including for example EPA food contact sanitizers requiring at least a 5 log reduction in pathogenic microorganisms in 30 seconds and/or NSF standards similarly requiring at least a 5 log reduction in treated pathogenic microorganisms. In still further aspects, without limiting the scope of the disclosure, the methods of the disclosure may provide sufficient sanitizing efficacy at conditions more or less strenuous than such regulatory standards.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The various methods of sanitizing rinsing according to the disclosure can include the use of any suitable level of the amine-based surfactant and defoaming agent. In some embodiments, the treated target composition comprises from about 1 ppm to about 1000 ppm of the amine-based surfactant when diluted for use. In further embodiments, the treated target composition comprises from about 1 ppm and about 100 ppm, 5 ppm and about 100 ppm, 10 ppm and about 100 ppm, 20 ppm and about 100 ppm, 25 ppm and about 100 ppm, 10 ppm and about 75 ppm, 20 ppm and about 75 ppm, 25 ppm and about 75 ppm, or about 25 ppm of the amine based surfactant when diluted for use. In further embodiments, the treated target composition comprises from about 1 ppm and about 500 ppm, 5 ppm and about 250 ppm, 10 ppm and about 100 ppm, 20 ppm and about 100 ppm, 25 ppm and about 100 ppm, 10 ppm and about 50 ppm, 20 ppm and about 50 ppm, 25 ppm and about 50 ppm, or about 50 ppm and about 100 ppm of the defoaming agent when diluted for use.

The various applications of use described herein provide the amine surfactant compositions to a surface and/or product in need of sanitizing and rinsing. Beneficially, the compositions of the disclosure are fast-acting. However, the present methods require a certain minimal contact time of the compositions with the surface or product in need of treatment for occurrence of sufficient antimicrobial effect. The contact time can vary with concentration of the use compositions, method of applying the use compositions, temperature of the use compositions, pH of the use compositions, amount of the surface or product to be treated, amount of soil or substrates on/in the surface or product to be treated, or the like. The contact or exposure time can be about 15 seconds, at least about 15 seconds, about 30 seconds or greater than 30 seconds. In some embodiments, the exposure time is about 1 to 5 minutes. In other embodiments, the exposure time is a few minutes to hours. In other embodiments, the exposure time is a few hours to days. The contact time will further vary based upon the use concentration of actives of compositions according to the disclosure.

The present methods can be conducted at any suitable temperature. In some embodiments, the present methods are conducted at a temperature ranging from about 0° C. to about 5° C., e.g., from about 5° C. to about 10° C., 0° C. to about 10° C., 0° C. to about 20° C., 0° C. to about 40° C., 0° C. to about 50° C., 0° C. to about 80° C., or at increased temperatures there above suitable for a particular application of use.

Beneficially, the 2-in-1 sanitizing rinse compositions are suitable for antimicrobial efficacy against a broad spectrum of microorganisms, providing broad spectrum bactericidal and fungistatic activity. For example, the of this disclosure provide broad spectrum activity against wide range of different types of microorganisms (including both aerobic and anaerobic microorganisms, gram positive and gram-negative microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one log 10. In other embodiments, the present methods can be used to reduce the microbial population in and/or on the target or the treated target composition by at least two log 10. In still other embodiments, the present methods can be used to reduce the microbial population in and/or on the target or the treated target composition by at least three log 10. In still other embodiments, the present methods can be used to reduce the microbial population in and/or on the target or the treated target composition by at least five log 10. Without limiting the scope of disclosure, the numeric ranges are inclusive of the numbers defining the range and include each integer within the defined range.

In an aspect, the methods of the disclosure include generating a use solution from the concentrated solid or liquid compositions of the disclosure. A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent and can vary from one location to another. The typical dilution factor is between about 1 and about 10,000. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In an aspect, a concentrated 2-in-1 sanitizing rinse composition is diluted to use solution concentration of about 0.001% (wt/vol.) to about 10% (wt/vol.), or from about 0.001% (wt/vol.) to about 5% (wt/vol.), or from about 0.001% (wt/vol.) to about 2% (wt/vol.), or from about 0.01% (wt/vol.) to about 1% (wt/vol.). Without being limited to a particular dilution of the concentrated 2-in-1 sanitizing rinse composition, in some aspects this dilution corresponds to approximately 0.1 mL to about 10 mL of the liquid concentrate per dish machine cycle (as one skilled in the art understands to further dependent on the rinse water volume of the dish machine). Without limiting the scope of disclosure, the numeric ranges are inclusive of the numbers defining the range and include each integer within the defined range.

Compositions of the disclosure can be formulated and sold for use as is, or as solvent or solid concentrates. If desired, such concentrates can be used full-strength as sanitizing rinse compositions. However, the concentrates typically will be diluted with a fluid (e.g., water) that subsequently forms the dilute phase or a use solution. Preferably, the concentrate forms a single phase before such dilution and remains so while stored in the container in which it will be sold. When combined with water or other desired diluting fluid at an appropriate dilution level and subjected to mild agitation (e.g., by stirring or pumping the composition), some compositions of the disclosure will form a pseudo-stable dispersion, and other compositions of the disclosure will form a clear or quasi-stable solution or dispersion. If a pseudo-stable composition is formed, then the composition preferably remains in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a suitable vessel, and preferably lasts for five minutes or more after mixing. Often normal refilling or replenishment of the applicator (e.g., by dipping the applicator in the composition) will provide sufficient agitation to preserve the pseudo-stable state of the composition during application.

The compositions can be dosed into an application of use, or dispensed as the concentrate or use solution, during a rinse application, such as a rinse cycle, for example, in a warewashing machine, a car wash application, or the like. In some embodiments, formation of a use solution can occur from a 2-in-1 sanitizing rinse composition installed in a cleaning machine, for example onto a dish rack. The 2-in-1 sanitizing rinse composition can be diluted and dispensed from a dispenser mounted on or in the machine or from a separate dispenser that is mounted separately but cooperatively with the dish machine. For example, in some embodiments, liquid rinse agents can be dispensed by incorporating compatible packaging containing the liquid material into a dispenser adapted to diluting the liquid with water to a final use concentration.

In other example embodiments, solid products may be conveniently dispensed by inserting a solid material in a container or with no enclosure into a spray-type dispenser Such a dispenser my incorporate with a warewashing machine in the rinse cycle. When demanded by the machine, the dispenser directs a spray of water onto the cast solid block of rinse agent which effectively dissolves a portion of the block creating a concentrated aqueous rinse solution which is then fed directly into the rinse water forming the aqueous rinse. The aqueous rinse is then contacted with the dishes to affect a complete rinse. This dispenser and other similar dispensers are capable of controlling the effective concentration of the active portion in the aqueous rinse by measuring the volume of material dispensed, the actual concentration of the material in the rinse water (an electrolyte measured with an electrode) or by measuring the time of the spray on the cast block. In general, the concentration of active portion in the aqueous rinse is preferably the same as identified above for liquid rinse agents. Some other embodiments of spray-type dispenser are disclosed in U.S. Pat. Nos. 4,826,661, 4,690,305, 4,687,121, 4,426,362 and in U.S. Pat. Nos. Re 32,763 and 32,818, the disclosures of which are incorporated by reference herein. An example of a particular product shape is shown in FIG. 9 of U.S. Pat. No. 6,258,765, which is incorporated herein by reference.

Additional Applications of Use

The sanitizing rinse composition comprising the amine surfactant compositions providing antimicrobial efficacy are further suitable for use in rinsing and wetting applications (including non-sanitizing applications), formation of ionic liquids, other antimicrobial and hard surface cleaning applications, formation of antimicrobial emulsions and micro-emulsion formations, dissolution and de-odorization of fatty acids, including carboxylates, such as disclosed as suitable anionics according to embodiments of the disclosure, and other enhanced antimicrobial applications (e.g. sanitizers, disinfectants, high level disinfectant for medical instruments, etc.).

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

Methods of Manufacture

The detergent compositions disclosed herein can be formed by combining the components in the weight percentages and ratios disclosed herein. The detergent compositions disclosed herein can be provided as a liquid or solid and a use solution is formed during the warewashing processes (or other application of use).

In some embodiments, compositions of the disclosure are prepared by simple addition of materials.

In other embodiments, the compositions according to the disclosure can be made by combining the components in an aqueous diluent using commonly available containers and blending apparatus. Beneficially, no special manufacturing equipment is required for making the compositions employing the amine-based surfactant and defoaming agent. A preferred method for manufacturing the cleaning composition of the disclosure includes introducing the components into a stirred production vessel.

Solid detergent compositions disclosed herein can be formed using the solidification matrix and are produced using a batch or continuous mixing system. In an exemplary embodiment, a single- or twin-screw extruder is used to combine and mix one or more agents at high shear to form a homogeneous mixture. In some embodiments, the processing temperature is at or below the melting temperature of the components. The processed mixture may be dispensed from the mixer by forming, casting or other suitable means, whereupon the detergent composition hardens to a solid form. The structure of the matrix may be characterized according to its hardness, melting point, material distribution, crystal structure, and other like properties according to known methods in the art.

Generally, a solid detergent composition processed according to the method of the disclosure is substantially homogeneous with regard to the distribution of ingredients throughout its mass and is dimensionally stable.

Specifically, in a forming process, the liquid and solid components are introduced into the final mixing system and are continuously mixed until the components form a substantially homogeneous semi-solid mixture in which the components are distributed throughout its mass. In an exemplary embodiment, the components are mixed in the mixing system for at least approximately 5 seconds. The mixture is then discharged from the mixing system into, or through, a die or other shaping means. The product is then packaged. In an exemplary embodiment, the formed composition begins to harden to a solid form in between approximately 1 minute and approximately 3 hours. Particularly, the formed composition begins to harden to a solid form in between approximately 1 minute and approximately 2 hours. More particularly, the formed composition begins to harden to a solid form in between approximately 1 minute and approximately 20 minutes.

Pressing can employ low pressures compared to conventional pressures used to form tablets or other conventional solid compositions. For example, in an embodiment, the present method employs a pressure on the solid of only less than or equal to about 5000 psi. In certain embodiments, the present method employs pressures of less than or equal to about 3500 psi, less than or equal to about 2500 psi, less than or equal to about 2000 psi, or less than or equal to about 1000 psi. In certain embodiments, the present method can employ pressures of about 1 to about 1000 psi, about 2 to about 900 psi, about 5 psi to about 800 psi, or about 10 psi to about 700 psi.

Specifically, in a casting process, the liquid and solid components are introduced into the final mixing system and are continuously mixed until the components form a substantially homogeneous liquid mixture in which the components are distributed throughout its mass. In an exemplary embodiment, the components are mixed in the mixing system for at least approximately 60 seconds. Once the mixing is complete, the product is transferred to a packaging container where solidification takes place. In an exemplary embodiment, the cast composition begins to harden to a solid form in between approximately 1 minute and approximately 3 hours. Particularly, the cast composition begins to harden to a solid form in between approximately 1 minute and approximately 2 hours. More particularly, the cast composition begins to harden to a solid form in between approximately 1 minute and approximately 20 minutes.

By the term "solid form", it is meant that the hardened composition will not flow and will substantially retain its shape under moderate stress or pressure or mere gravity. The degree of hardness of the solid cast composition may range from that of a fused solid product which is relatively dense and hard, for example, like concrete, to a consistency characterized as being a hardened paste. In addition, the term "solid" refers to the state of the detergent composition under the expected conditions of storage and use of the solid detergent composition. In general, it is expected that the detergent composition will remain in solid form when exposed to temperatures of up to approximately 100° F. and particularly greater than approximately 120° F.

The resulting solid detergent composition may take forms including, but not limited to: a pressed solid; a cast solid product; an extruded, molded or formed solid pellet, block, tablet, powder, granule, flake; or the formed solid can thereafter be ground or formed into a powder, granule, or flake. In an exemplary embodiment, extruded pellet materials formed by the solidification matrix have a weight of between approximately 50 grams and approximately 250 grams, extruded solids formed by the solidification matrix have a weight of approximately 100 grams or greater, and solid block detergents formed by the solidification matrix have a mass of between approximately 1 and approximately 10 kilograms. The solid compositions provide for a stabilized source of functional materials. In some embodiments, the solid composition may be dissolved, for example, in an aqueous or other medium, to create a concentrated and/or use solution. The solution may be directed to a storage reservoir for later use and/or dilution or may be applied directly to a point of use. Alternatively, the solid alkaline detergent composition is provided in the form of a unit dose, typically provided as a cast solid, an extruded pellet, or a tablet having a size of between approximately 1 gram and approximately 100 grams. In another alternative, multiple-use solids can be provided, such as a block or a plurality of pellets, and can be repeatedly used to generate aqueous detergent compositions for multiple cycles.

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

EXAMPLES

Embodiments of the detergent compositions disclosed herein are further defined in the following non-limiting Examples. It should be understood that these Examples, while indicating certain embodiments of the detergent compositions disclosed herein, are given by way of illustration only. From the above discussion and these Examples, one skilled in the art can ascertain the essential characteristics of the detergent compositions disclosed herein, and without departing from the spirit and scope thereof, can make various changes and modifications of the embodiments of the detergent compositions disclosed herein to adapt it to various usages and conditions. Thus, various modifications of the embodiments of the detergent compositions disclosed herein, in addition to those shown and described herein, will be apparent to those skilled in the art from the foregoing description. Such modifications are also intended to fall within the scope of the appended claims.

Example 1

In order to first determine if the amine based surfactants can sufficiently reduce the surface tension in order to function as a cleaning/rinse aid, the critical micelle concentrations (CMC) of various concentrations of either a single amine surfactant, bis(3-aminopropyl)dodecylamine, or a mixture of amine surfactants exemplified by an amie mix of N—$C_{10-16}$-alkyltrimethylenediamine reaction products with chloroacetic acid, at various pHs was determined.

All samples were run on a tensiometer with the concentration of the amine surfactants ranging from 0.001 to 1 wt % in up to 50 mL DI water. The pH of the solution was changed for each range of concentrations of the bis(3-aminopropyl)dodecylamine or the mix of N—$C_{10-16}$-alkyltrimethylenediamine reaction products with chloroacetic acid and set to a pH of 5, 7, and 9 to determine any possible effects that an acidic, neutral, or basic environment may have on the performance of the amine surfactants.

Figure 2:
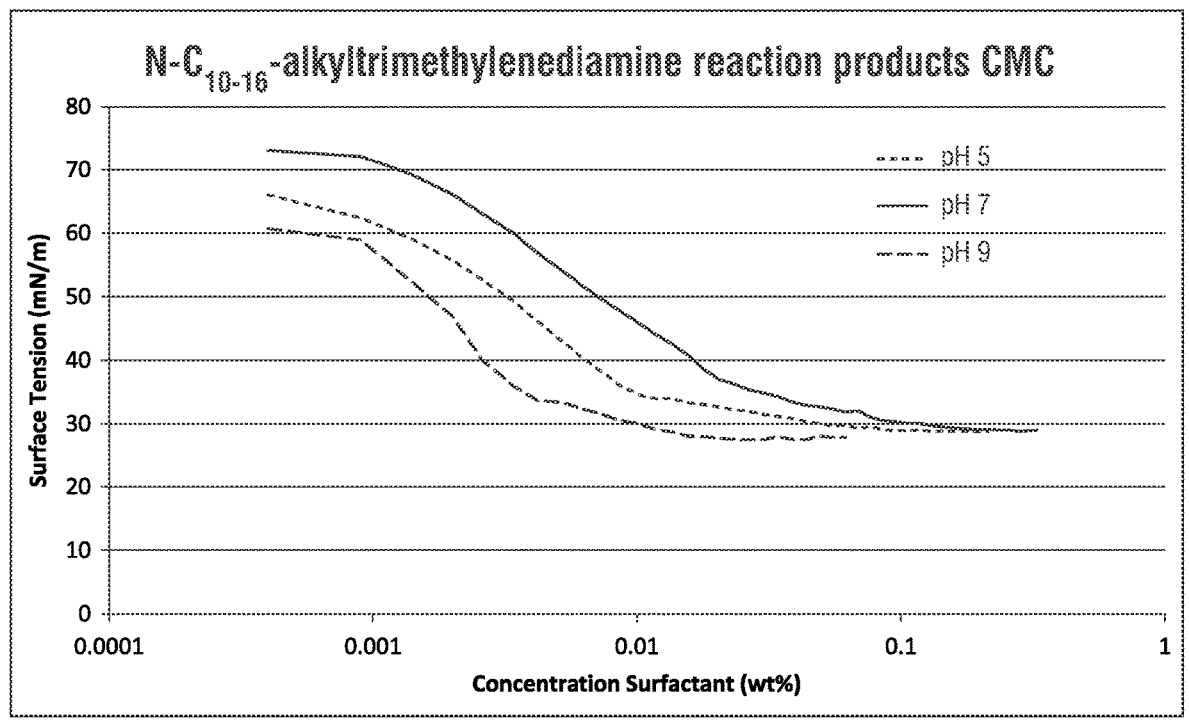
FIG. 2 is a graphical representation of the critical micelle plots of the amine surfactant N-alkyl aminopropyl glycine showing a pH dependent response with respect to CMC likely due to, as the pH shifts from alkaline pH 9, to neutral pH 7, and finally pH 5, the amine based surfactant is becoming more cationic (protonated) in nature resulting in higher electrostatic repulsion, and raising the CMC by an order of magnitude.

As can be seen in FIGS. 1 and 2, both bis(3-aminopropyl)dodecylamine and the mix of N—$C_{10-16}$-alkyltrimethylenediamine reaction products with chloroacetic acid were capable of significantly reducing the surface tension of the water at each pH. bis(3-aminopropyl)dodecylamine was capable of reducing the surface tension to about 35 mN/m at a pH of 5 and 7 and about 32 mN/m at a pH of 9 (FIG. 1). The mix of N—$C_{10-16}$-alkyltrimethylenediamine reaction products with chloroacetic acid was able to further lower the surface tension to below 30 mN/m (FIG. 2).

Further, both compositions show a pH dependent curve. As can be seen in FIGS. 1 and 2, by raising the pH, both bis(3-aminopropyl)dodecylamine and the mix of N—$C_{10-16}$-alkyltrimethylenediamine reaction products with chloroacetic acid showed an increase in its ability to lower surface tension at reduced concentrations (lower CMC value). Without being bound by theory, it is believed that as the pH shifts from an alkaline, e.g. pH 9, to neutral pH 7, to acidic, e.g. pH 5, the amine based surfactants are becoming more cationic (protonated) in nature resulting in higher electrostatic repulsion, and raising the CMC by an order of magnitude.

Example 2

In order to determine the efficacy of the amine-based surfactants in various environments as determined by different pH values, the surfactants were tested for antimicrobial efficacy on *E. coli* and *Staphylococcus aureus*. Following the AOAC Official Method 960.09 (Germicidal and Detergent Sanitizing Action of Disinfectants), compositions were tested at about pH 5, about pH 7, and about pH 9 at concentrations ranging from about 12.5 to about 400 ppm (FIGS. 3-5 for bis(3-aminopropyl)dodecylamine and FIGS. 6-8 for the mix of N—$C_{10-16}$-alkyltrimethylenediamine reaction products with chloroacetic acid).

Figure 3:
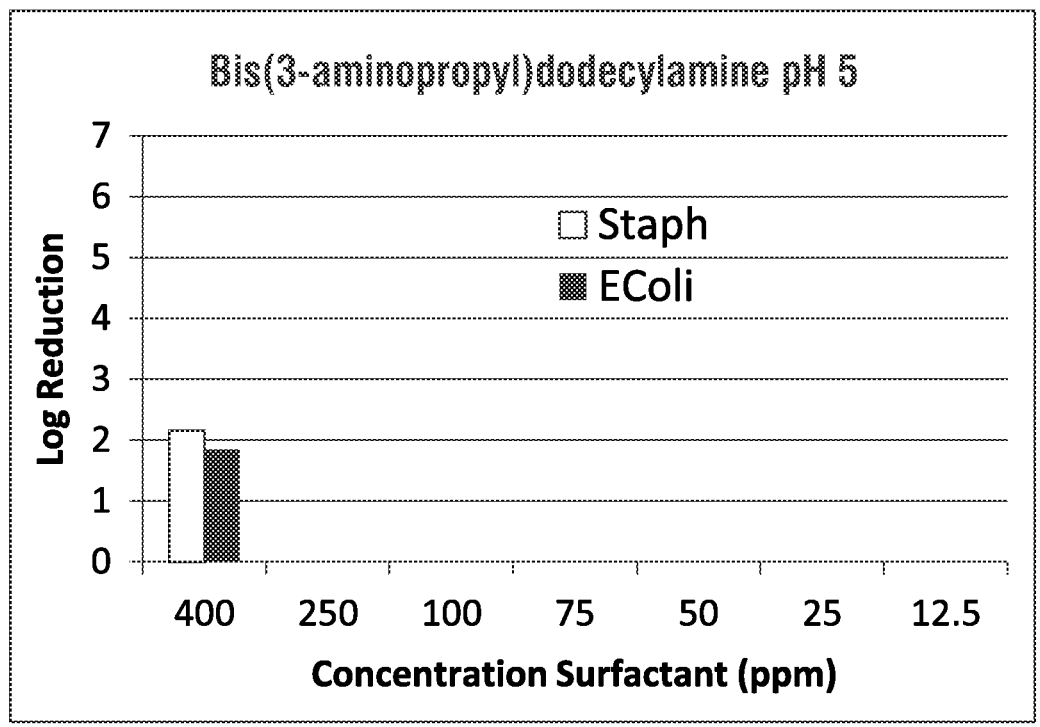
FIG. 3 is a graphical representation of the antimicrobial potency of bis(3-aminopropyl) dodecylamine at a pH of 5 as expressed by the log reduction of Staphylococcus aureus and E. coli.
Figure 4:
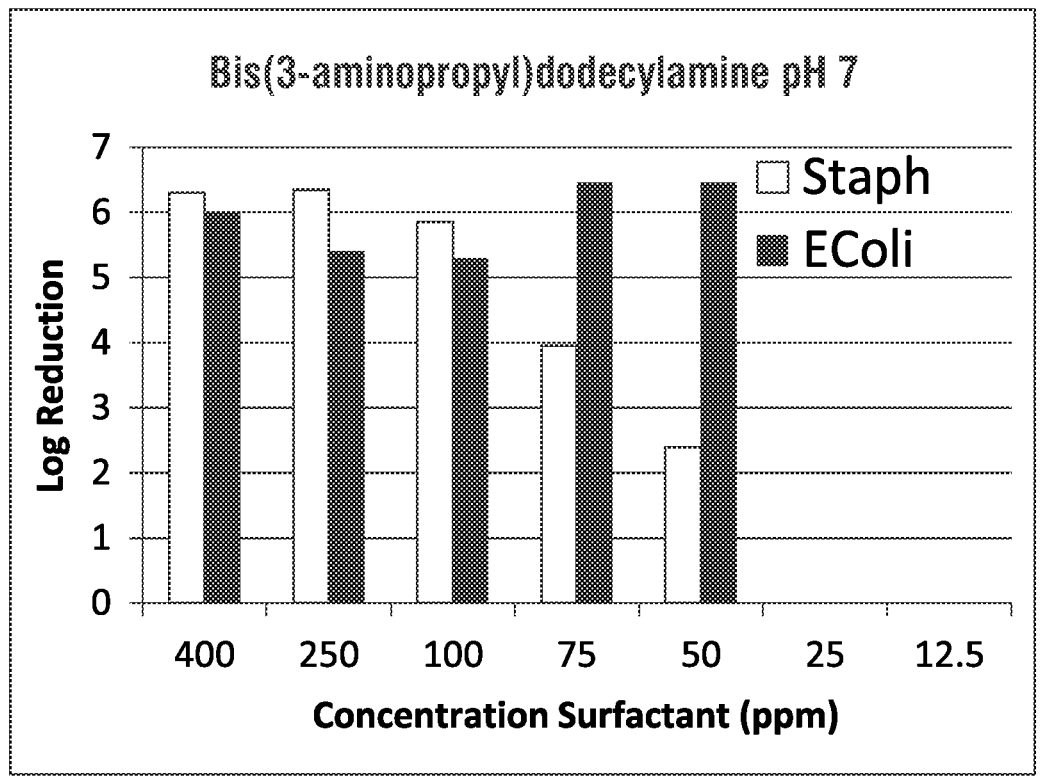
FIG. 4 is a graphical representation of the antimicrobial potency of bis(3-aminopropyl) dodecylamine at a pH of 7 as expressed by the log reduction of Staphylococcus aureus and E. coli.
Figure 5:
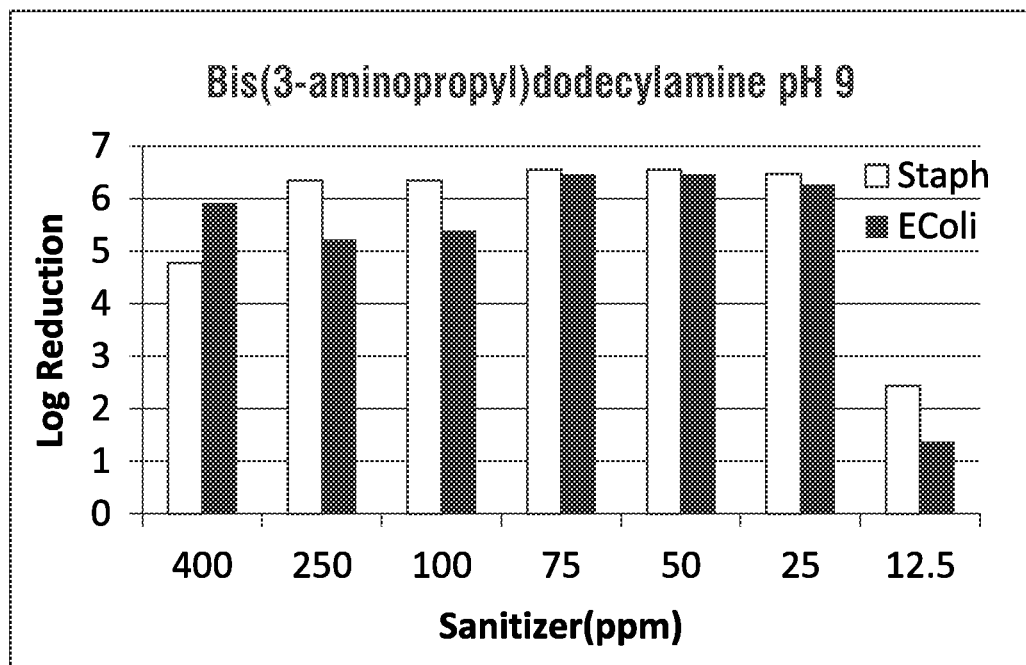
FIG. 5 is a graphical representation of the antimicrobial potency of bis(3-aminopropyl) dodecylamine at a pH of 9 as expressed by the log reduction of Staphylococcus aureus and E. coli.
Figure 6:
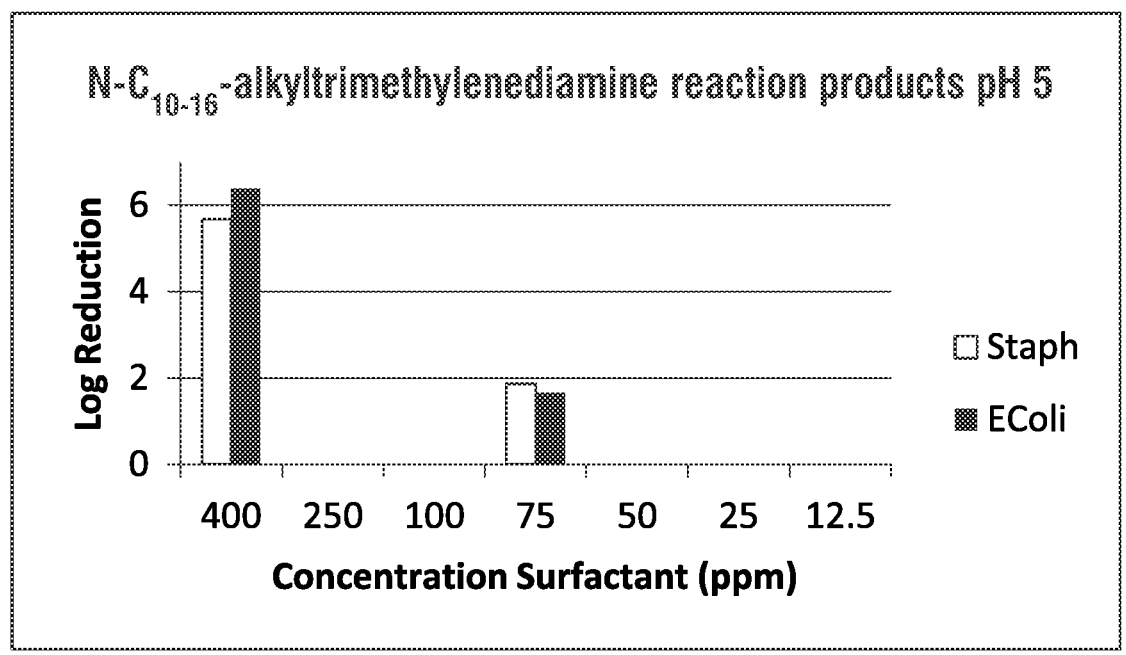
FIG. 6 is a graphical representation of the antimicrobial potency of an amine surfactant mix at a pH of 5 as expressed by the log reduction of Staphylococcus aureus and E. coli.
Figure 7:
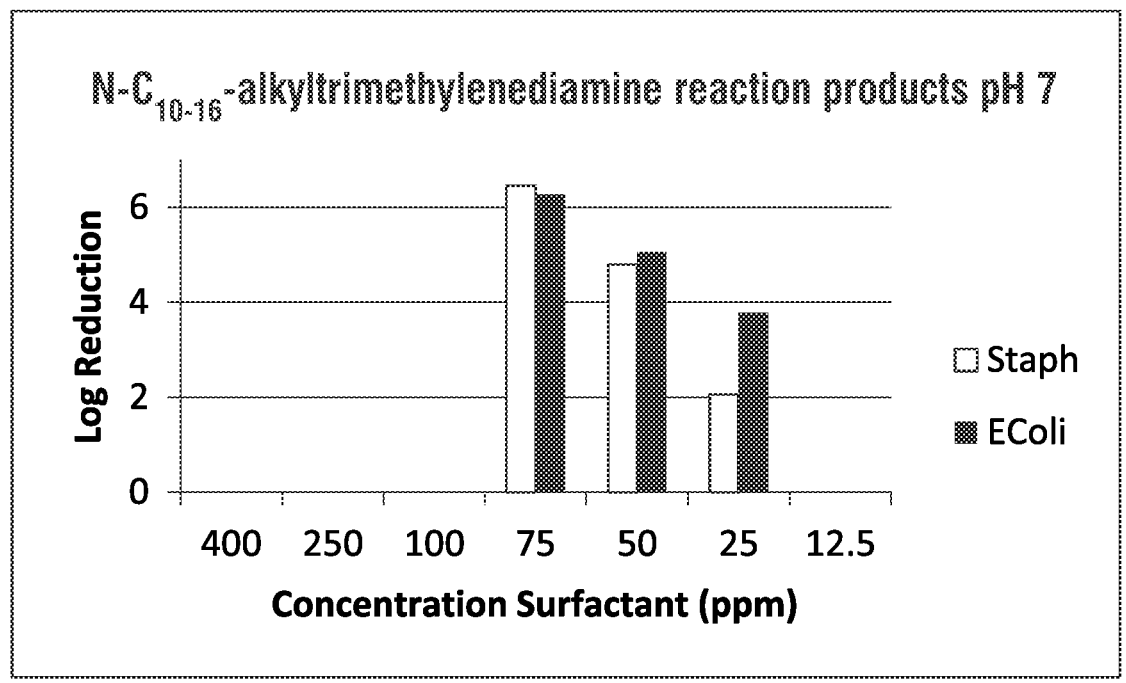
FIG. 7 is a graphical representation of the antimicrobial potency of an amine surfactant mix at a pH of 7 as expressed by the log reduction of Staphylococcus aureus and E. coli.

As can be seen for both bis(3-aminopropyl)dodecylamine and the mix of N—$C_{10-16}$-alkyltrimethylenediamine reaction products with chloroacetic acid, there is a pH dependent effect on log reduction of the bacteria. At a pH of 5, only the mix of N—$C_{10-16}$-alkyltrimethylenediamine reaction products with chloroacetic acid was able to achieve a 5-log reduction in both *E. coli* and *Staphylococcus aureus*, and only at the highest concentration tested (FIGS. 3 and 6). However, as the pH increased from 5 to 7 to 9, the efficacy of both bis(3-aminopropyl)dodecylamine and the mix of N—$C_{10-16}$-alkyltrimethylenediamine reaction products with chloroacetic acid increased for both *E. coli* and *Staphylococcus aureus*.

Figure 8:
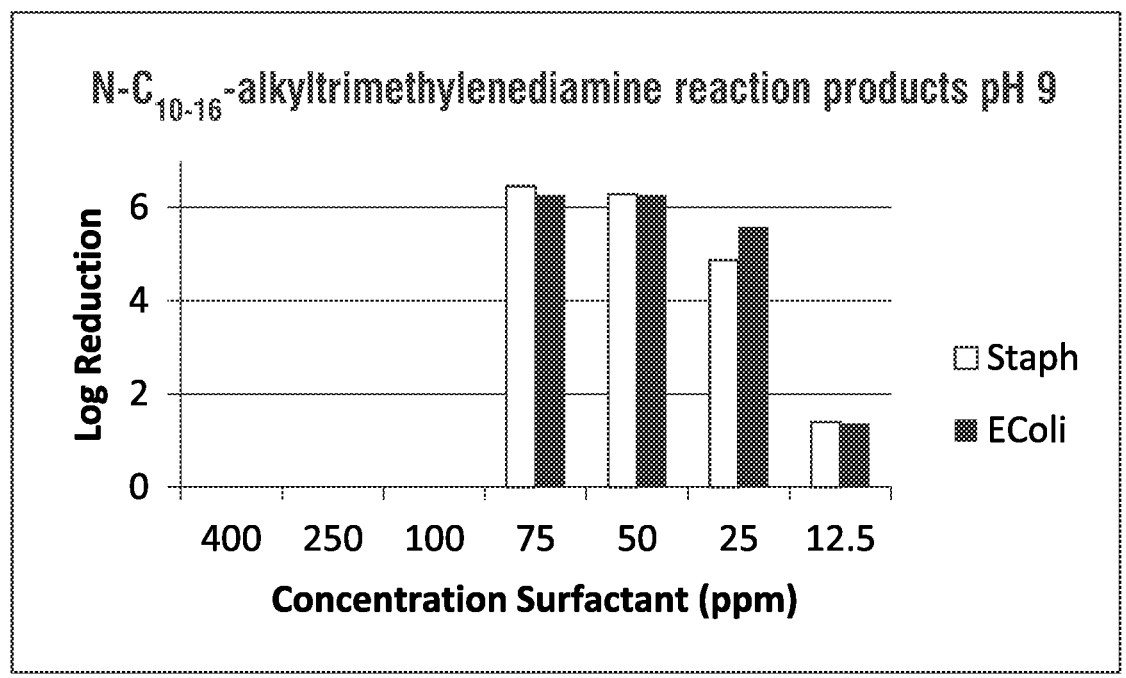
FIG. 8 is a graphical representation of the antimicrobial potency of an amine surfactant mix at a pH of 9 as expressed by the log reduction of Staphylococcus aureus and E. coli.

When testing efficacy at pH 7 (FIGS. 4 and 7), both bis(3-aminopropyl)dodecylamine and the mix of N—$C_{10-16}$-alkyltrimethylenediamine reaction products with chloroacetic acid were able to achieve a 5-log reduction on *E. coli* down to a concentration of 50 ppm. However, against *Staphylococcus aureus*, bis(3-aminopropyl)dodecylamine needed a concentration between 75 and 100 ppm (FIG. 4) while the mix of N—$C_{10-16}$-alkyltrimethylenediamine reaction products with chloroacetic acid needed a concentration between 50 and 75 ppm (FIG. 7) to achieve the 5-log reduction. At pH 9, bis(3-aminopropyl)dodecylamine achieved a 5 log reduction for both *E. coli* and *Staphylococcus aureus* at a concentration between 12.5 and 25 ppm (FIG. 5), while the mix of N—$C_{10-16}$-alkyltrimethylenediamine reaction products with chloroacetic acid needed a concentration between 25 and 50 for a 5 log reduction in *Staphylococcus aureus* and between 12.5 and 25 ppm for *E. coli* (FIG. 8).

As can be seen by these results, both surfactant compositions show a pH dependent response for microbial efficacy, with better performance as the compositions become more basic. As the pH becomes more neutral and slightly acidic (pH 5), the efficacy drops off requiring a higher concentration to achieve at least a 5-log reduction in bacteria. This is in agreement with the increased efficacy at reducing surface tension with an increase in pH as seen in Example 1.

Example 3

The ability of a defoaming agent to control the foaming profile of the surfactant was also tested. As bis(3-aminopropyl)dodecylamine showed good antimicrobial properties at 25 ppm at pH 9 in Example 2 against both *E. coli* and *Staphylococcus aureus*, it was tested at 25 ppm at pH 8.5 across different ratios with an alkoxylated alkyl alcohol nonionic defoaming agent at 100 or 120° F. using the Glewwe foam test.

As shown in Table 2, fatty alcohol alkoxylate (an alkoxylated alkyl alcohol nonionic surfactant) defoaming agent can efficiently suppress foam of bis(3-aminopropyl)dodecylamine and even defoam food soil in combination with the amine-based sanitizing surfactant. The foam height never surpassed the maximum height of 3 inches allowed by the Glewwe test for a passing test and generally had no foam or a low froth present. Even at a 3:1 ratio of surfactant to defoamer, the fatty alcohol alkoxylate was sufficient to keep the foam low for machine ware washing. At lower ratios, such as 2:1 or 1:1 surfactant to defoamer, the level of foam was even better maintained at a low to nonexistent amount.

Example 4

As the other Examples show the anime-based surfactants having a sensitivity to pH in their properties, including their antimicrobial efficacy, it was unknown how mixing them with a defoaming agent would affect their antimicrobial efficacy. Following the same protocol as in Example 2, bis(3-aminopropyl)dodecylamine and the fatty alcohol alkoxylate (alkoxylated alkyl alcohol nonionic surfactant) defoaming agent at different concentrations and ratios was tested at pH 9 (FIG. 9).

As shown in FIG. 9. the surfactant and defoamer blends were able to achieve at least a 5-log reduction in both *E. coli* and *Staphylococcus aureus* at concentrations below 60 ppm with a 2:1 ratio of surfactant to defoamer. However, at a 1:1 ratio with 50 ppm bis(3-aminopropyl)dodecylamine, only a 2.4 log reduction for *Staphylococcus aureus* and a 3.7 log reduction for *E. coli* was achieved. Therefore, at low concentrations of the amine-based surfactant, a higher ratio of surfactant to defoamer is needed in order to have an antimicrobial effect.

Example 5

Compatibility of the compositions of this disclosure was further tested with other compounds, such as enzymes. Initial tests were done using individual or combinations of neutral detergent, enzyme, and/or an amine surfactant as shown in FIG. 10. The wares were washed for 7 cycles and the protein film remaining was assessed, with 1 being the best detergency and 5 being the worst. As shown in FIG. 10, the bis(3-aminopropyl)dodecylamine based rinse aid alone or in combination with the neutral pH detergent had a poor performance in the removal of protein. With the addition of about 10 ppm of a protease, there was a slight improvement when combined with the detergent and amine surfactant. However, the improvement was less than just the enzyme and detergent alone, which had the best detergency of the different combinations. Therefore, at a neutral pH, even with

TABLE 2

Glewwe testing using bis(3-aminopropyl)dodecylamine and fatty alcohol alkoxylate

| | Temp (F.) | Rinse Aid (g) | % Active Sanitizer | % Active Defoamer | ppm Sanitizer | ppm Defoamer | Surfactant Foam Profile | | | Powdered Milk Protein Soil | | |
|---|---|---|---|---|---|---|---|---|---|---|---|---|
| | | | | | | | 0 min | 15 sec | 1 min | 0 min | 15 sec | 1 min |
| 25 ppm bis(3-aminopropyl)dodecylamine, pH 8.5 | 120 | 0.075 | 100.0 | 0 | 25 | 0 | 9 | 9 | 8 | — | — | — |
| 1:1 bis(3-aminopropyl)dodecylamine/ fatty alcohol alkoxylate | 120 | 0.15 | 50 | 50 | 25 | 25 | 0 | 0 | 0 | 0 | 0 | 0 |
| 2:1 bis(3-aminopropyl)dodecylamine/ fatty alcohol alkoxylate | 120 | 0.1125 | 66.67 | 33.37 | 37.5 | 12.5 | 1¼ | ¼ (froth) | 0 | 1 | 0 | 0 |
| 3:1 bis(3-aminopropyl)dodecylamine/ fatty alcohol alkoxylate | 120 | 0.099 | 75 | 25 | 33.3 | 16.7 | ¼ (froth) | ½ | ¼ (froth) | 2½ | 1½ | 0 (large air bubbles) |
| 1:1 bis(3-aminopropyl)dodecylamine/ fatty alcohol alkoxylate | 100 | 0.15 | 50 | 50 | 25 | 25 | ½ | 0 | 0 | ⅛ (froth) | 0 | 0 |
| 2:1 bis(3-aminopropyl)dodecylamine/ fatty alcohol alkoxylate | 100 | 0.1125 | 66.67 | 33.33 | 37.5 | 12.5 | 1 | ¼ (froth) | 0 | 1 | 0 | 0 | an enzyme, the amine surfactant has a worse performance than just detergent alone, or detergent plus an enzyme.

However, as shown in previous Examples, the amine surfactants have a pH dependency for their properties which may be due to their protonation at lower pH values. It was also shown in Example 2 that at higher pH values, the amine surfactant has a higher antimicrobial effect and Example 1 showed that at a more basic pH, the bis(3-aminopropyl) dodecylamine has a lowered critical micelle concentration. Therefore, to retain their antimicrobial properties, the amine surfactants were tested at increasing pH detergents combined with an enzyme for their rinse aid properties on proteinaceous soils.

As shown in FIG. 11, as pH is increased from about pH 9 to pH 11 with about 10 ppm enzyme (a protease at pH 9 and lower, an endopeptidase at pH 10 and higher), the ability to remove protein increases. Further, between about a pH of 10 and a pH of 10.5, the ability of the detergent, endopeptidase, and bis(3-aminopropyl)dodecylamine prevented nearly any film formations, having a score of 1. Taken together with the previous Examples, in order to maintain a good antimicrobial efficacy as well as other properties, the pH should be slightly basic and above about 25 ppm of the amine surfactant should be included in the compositions of the disclosure.

The disclosures being thus described, it will be obvious that the same may be varied in many ways. Such variations are not to be regarded as a departure from the spirit and scope of the disclosures and all such modifications are intended to be included within the scope of the following claims. The above specification provides a description of the manufacture and use of the disclosed compositions and methods. Since many embodiments can be made without departing from the spirit and scope of the disclosure, the disclosure resides in the claims.

What is claimed is:

1. A sanitizing cleaning/rinse aid composition comprising: one or more amine surfactants having the formula:

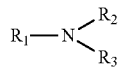

wherein group $R_1$ is a linear or branched, saturated or unsaturated $C_4$-$C_{24}$ alkyl group or H; and
$R_2$ and $R_3$ are selected from the group of H, $(CH_2)_3NH_2$, $(CH_2)_3NHCH_2COOH$, $CH_2COOH$, $(CH_2)_3N(CH_2COOH)_2$, $(CH_2)_3NH_2$;
a defoaming agent comprising a fatty alcohol alkoxylate; and
an alkalinity source comprising an alkali metal carbonate;
wherein the molar ratio of defoaming agent to amine surfactant is from about 1:1 to about 1:3,
and wherein said composition is substantially free of chlorine, oxidizers, and/or quaternary ammonium chloride.

2. The sanitizing cleaning/rinse aid composition of claim 1 further comprising an enzyme.

3. The sanitizing cleaning/rinse aid composition of claim 1, wherein the amine surfactants are one or more of:
N-alkylaminopropyl glycerin, bis(3-aminopropyl) dodecylamine,

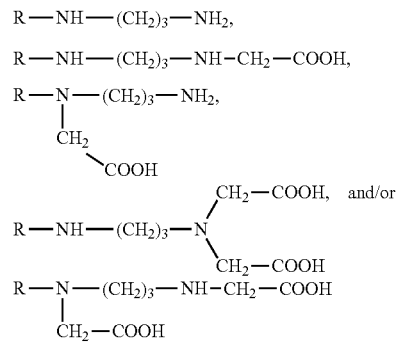

where R has a carbon chain length of 4-24.

4. The composition of claim 1, wherein the amine surfactant is comprised of N-alkylaminopropyl glycerin, bis(3-aminopropyl) dodecylamine, N—$C_{10-16}$-alkyltrimethylenediamine reaction products with chloroacetic acid, and/or combinations thereof.

5. The composition of claim 1, wherein $R_1$ has a carbon chain length of 6-18 carbon atoms.

6. The composition of claim 1, wherein the pH of a use solution is between about 9 and about 11.

7. The composition of claim 1, wherein the composition is soluble in water and provides in a use solution from about 20 ppm to about 400 ppm amine surfactant and from about 10 ppm and about 400 ppm defoaming agent.

8. The composition of claim 1, wherein the composition is substantially free of chlorine, oxidizers, and quaternary ammonium chloride.

9. The composition of claim 1, further comprising an additional functional ingredient selected from the group consisting of additional surfactants, thickeners and/or viscosity modifiers, solvents, solubility modifiers, humectants, metal protecting agents, stabilizing agents, corrosion inhibitors, sequestrants and/or chelating agents, solidifying agent, sheeting agents, fragrances and/or dyes, hydrotropes, couplers, buffers, and combinations thereof.

10. The composition of claim 2, wherein the enzyme is a protease.

11. A cleaning/rinse aid composition with sanitizing activity comprising:
from about 0.001 wt. % to about 95 wt. % of an amine surfactant;
from about 0.001 to about 50 wt. % of a defoaming surfactant comprising a fatty alcohol alkoxylate;
an alkalinity source comprising an alkali metal carbonate; and
optional additional functional ingredients up to about 80 wt. % or one or more of additional surfactant, builders, enzymes, thickeners and/or viscosity modifiers, solvents, solubility modifiers, humectants, metal protecting agents, stabilizing agents, corrosion inhibitors, sequestrants, chelating agents, solidifying agents, sheeting agents, hydrotropes, couplers, and/or buffers;
wherein the molar ratio of defoaming surfactant to amine surfactant is from about 1:1 to about 1:3, and wherein said composition is substantially free of chlorine, oxidizers, and/or quaternary ammonium chloride.

12. The cleaning/rinse aid composition of claim 11 further comprising a builder or enzyme.

13. A method of sanitizing a surface with a cleaning/rinse aid composition comprising:
provAiding the composition of claim 1 to a surface; and
rinsing said composition from said surface
wherein said surface is sanitized without the need thereof of an additional rinsing step, and further wherein the sanitizing provides at least a 5-log microbial kill on the surface.

14. The method of claim 13, wherein the composition is mixed into an aqueous use solution prior to applying to the surface in need of cleaning and/or sanitizing.

15. The method of claim 13, further comprising diluting the composition to provide a use solution providing from about 25 ppm to about 400 ppm amine surfactant and from about 12.5 ppm and about 400 ppm defoaming agent.

16. The method of claim 13, wherein the sanitized surface is film-free and/or spot-free.

17. The method of claim 13, wherein the sanitizing efficacy is within 30 seconds of contacting the surface.

* * * * *